US008765096B2

(12) United States Patent
Leamon et al.

(10) Patent No.: US 8,765,096 B2
(45) Date of Patent: Jul. 1, 2014

(54) METHODS AND COMPOSITIONS FOR TREATING AND DIAGNOSING KIDNEY DISEASE

(75) Inventors: Christopher Paul Leamon, West Lafayette, IN (US); Iontcho Radoslavov Vlahov, West Lafayette, IN (US)

(73) Assignee: Endocyte, Inc, West Lafayette, IN (US)

( * ) Notice: Subject to any disclaimer, the term of this patent is extended or adjusted under 35 U.S.C. 154(b) by 0 days.

(21) Appl. No.: 13/440,641

(22) Filed: Apr. 5, 2012

(65) Prior Publication Data
US 2012/0270791 A1    Oct. 25, 2012

Related U.S. Application Data

(63) Continuation of application No. 12/527,316, filed as application No. PCT/US2008/054189 on Feb. 16, 2008.

(60) Provisional application No. 60/901,778, filed on Feb. 16, 2007.

(51) Int. Cl.
A61K 51/00    (2006.01)
A61M 36/14    (2006.01)
A61K 51/04    (2006.01)

(52) U.S. Cl.
CPC ....... *A61K 51/04* (2013.01); *A61K 51/00* (2013.01)
USPC ....... 424/1.69; 424/1.11; 424/1.65; 424/1.73; 424/9.1

(58) Field of Classification Search
CPC ....... A61K 51/04; A61K 51/00; A61K 51/06; A61K 51/065; A61K 51/0497; A61K 2123/00; A61K 38/00; A61K 2121/00
USPC ................. 424/1.11, 1.65, 1.73, 9.1, 9.2, 1.69
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Sirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Remy et al (Proceedings of the National Academy of Sciences of the United States of America, 1999, vol. 96, No. 10, pp. 5394-5399).*
Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.
Archer M.C. et al., "Separation of Folic Acid Derivatives and Pterins by High-Performance Liquid Chromatography," *Methods in Enzymology*, 1980; 66: pp. 452-459.

(Continued)

*Primary Examiner* — D L Jones
(74) *Attorney, Agent, or Firm* — Barnes & Thornburg LLP

(57) ABSTRACT

The invention relates to a method for diagnosing a kidney disease state. The method comprises the steps of administering to a patient a composition comprising a conjugate or complex of the general formula V-L-D where the group V comprises a vitamin receptor binding ligand that binds to kidney proximal tubule cells and the group D comprises a diagnostic marker, and diagnosing the kidney disease state. The invention also relates to a method for treating a kidney disease state. The method comprises the steps of administering to a patient suffering from the disease state an effective amount of a composition comprising a conjugate or complex of the general formula V-L-D where the group V comprises a vitamin receptor binding ligand that binds to kidney proximal tubule cells and the group D comprises an antigen, a cytotoxin, or a cell growth inhibitor, and eliminating the disease state.

8 Claims, 6 Drawing Sheets

(56) References Cited

U.S. PATENT DOCUMENTS

| | | |
|---|---|---|
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Fawzi et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,582,744 B2 | 9/2009 | Manoharan et al. |
| 7,601,332 B2 * | 10/2009 | Vlahov et al. ............ 424/1.73 |
| 8,476,451 B2 | 7/2013 | Ellman et al. |
| 2003/0086900 A1 | 5/2003 | Low et al. |
| 2003/0162234 A1 | 8/2003 | Jallad |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Manoharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2006/0105975 A1 | 5/2006 | Pendergrast et al. |
| 2006/0128754 A1 | 6/2006 | Hoefle et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2010/0004276 A1 | 1/2010 | Vlahov et al. |
| 2010/0048490 A1 | 2/2010 | Vlahov et al. |
| 2010/0104626 A1 | 4/2010 | Leamon et al. |
| 2010/0240701 A1 | 9/2010 | Vlahov et al. |
| 2010/0323973 A1 | 12/2010 | Leamon et al. |
| 2011/0028714 A1 | 2/2011 | Green et al. |
| 2011/0288152 A1 | 11/2011 | Low et al. |
| 2012/0065149 A1 | 3/2012 | Vlahov et al. |
| 2012/0258905 A1 | 10/2012 | Leamon et al. |
| 2012/0270791 A1 | 10/2012 | Leamon et al. |
| 2013/0116195 A1 | 5/2013 | Leamon et al. |
| 2013/0137139 A1 | 5/2013 | Vlahov et al. |
| 2013/0158271 A1 | 6/2013 | Vlahov et al. |
| 2013/0184435 A1 | 7/2013 | Vlahov et al. |
| 2013/0203680 A1 | 8/2013 | Leamon et al. |
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |

FOREIGN PATENT DOCUMENTS

| | | |
|---|---|---|
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO/85/05554 | 12/1985 |
| WO | WO 88/01622 | 3/1988 |
| WO | WO 90/12096 | 10/1990 |
| WO | WO 91/07418 | 5/1991 |
| WO | WO 96/36367 | 11/1996 |
| WO | WO 98/08859 | 3/1998 |
| WO | WO 98/10651 | 3/1998 |
| WO | WO 99/20626 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74382 | 10/2001 |
| WO | WO02/059272 | 8/2002 |
| WO | WO 02/085908 | 10/2002 |
| WO | WO 02/087424 | 11/2002 |
| WO | WO 2002/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO/2004/022099 | 3/2004 |
| WO | WO/2004/037210 | 5/2004 |
| WO | WO 2004/046170 | 6/2004 |
| WO | WO 2004/054622 | 7/2004 |
| WO | WO 2004/069159 | 8/2004 |
| WO | 2004/100983 | 11/2004 |
| WO | WO 2005/074901 | 8/2005 |
| WO | WO 2005/112919 | 12/2005 |
| WO | WO 2006/012527 | 2/2006 |
| WO | WO 2006/042146 | 4/2006 |
| WO | WO/2006/089007 | 8/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | WO 2008/057437 | 5/2008 |
| WO | WO 2008/101231 | 8/2008 |

(56) References Cited

FOREIGN PATENT DOCUMENTS

| WO | WO 2008/112873 | 9/2008 |
|---|---|---|
| WO | WO 2009/002993 | 12/2008 |
| WO | WO 2009/055562 | 4/2009 |
| WO | WO2011/069116 | 6/2011 |
| WO | WO2011/106639 | 9/2011 |
| WO | WO2012/019123 | 2/2012 |

OTHER PUBLICATIONS

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.
Ayers W.A., "Effect of Vitamin B12 and Analogs on the Respiration of a Marine Bacterium," *Archives of Biochemistry and Biophysics*, 1962, vol. 96, pp. 210-215.
Barnett C.J. et al., "Structure-Activity Relationships of Dimeric Catharanthus Alkaloids. 1. Deacetylvinblastine Amide (Vindesine) Sulfate," *J. Med. Chem*. 21: 88-96 (1978).
Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.
Bavetsias, V., et al., "The design and synthesis of water-soluble analogues of CB30865, a quinazolin-4-one-based antitumor agent," J Med Chem, 2002; 45(17): 3692-3702.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J Org. Chem.*, 1992; 57: 2873-2876.
Campbell et al., "Folate-binding protein is a marker for ovarian cancer," *Cancer Res.*, 1991; 51: 5329-5338.
Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsil)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid—polylysine-mediated introduction of c-*myb* antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
Domling A. et al., "Myxobacterial Epothilones and Tubulysins as Promising Anticancer Agents," *Molecular Diversity*, 2005; 9: 141-147.
Douglas J.T. et al., "Targeted Gene Delivery by Tropism-Modified Adenoviral Vectors," *Nat. Biotechnol.*, 1996, vol. 14, pp. 1574-1573.
Eichman, J.D. et al., "The Use of PAMAM Dendrimers as the Efficient Transfer of Genetic Material Into Cells", Jul. 2000, *PSTT*, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
Frankel AE., "Immunotoxin therapy of cancer," *Oncology*, 1993; 7(5): 69-78.

Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
U.S. Appl. No. 60/946,092, filed Jun. 25, 2007, Vlahov et al.
U.S. Appl. No. 60/982,595, filed Nov. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-*S*-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.
Hofland et al., "Folate-targeted gene transfer in vivo," *Mol Ther* 5(6): 739-744 (2002).
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Holladay et al., "Riboflavin-mediated delivery of a macromolecule into cultured human cells," *Biochim Biophys Acta*, 1426(1): 195-204 (1999).
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.
Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.

(56) References Cited

OTHER PUBLICATIONS

Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kim et al., "Synthesis and biological activity of 10-thia-10-deaza analogs of folic acid, pteroic acid, and related compounds", *Journal of Medical Chemistry*, 18: 776-780 (1975).
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in *Lactobacillus salivarius*. Characterization of the transport mechanism and purification and properties of the binding component," *J Biol. Chem..* 1987; 262(15):7171-7179.
Ladino et al., "Folate-maytansinoids: target-selective drugs of low molecular weight," *Int. J Cancer*, 73(6): 859 864 (1997).
Lambooy J. P., "Riboflavin Analogs Utilized for Metabolism by a *Lactobacillus casei* Mutant," *Int. J Biochem.*, vol. 16, No. 2, 1984, pp. 231-234.
Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Leamon CP et al, "Cytotoxicity of folate-Pseudomonas exotoxin conjugates toward tumor cells. Contribution of translocation domain," *J. Biol. Chem.* 268(33): 24847-24854 (1993).
U.S. Appl. No. 60/590,580, filed Jul. 23, 2004, Vlahov et al.
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.
Leamon CP et al., "Delivery of macromolecules into living cells: a method that exploits folate receptor endocytosis," *Proc. Natl. Acad Sci. USA* 88(13): 5572-5573 (1991).
Leamon CP et al., "Folate-mediated targeting: from diagnostics to drug and gene delivery," *Drug Discovery Today* 6: 44-51 (2001).
Leamon CP et al., "Folate-targeted chemotherapy," *Adv Drug Deliv Rev*, 2004;56(8): 1127-41.
Leamon CP et al., "Membrane folate-binding proteins are responsible for folate-protein conjugate endocytosis into cultured cells," *Biochem. J.* 291: 855-860 (1993).
Leamon CP et al., "Selective targeting of malignant cells with cytotoxin-folate conjugates," *J Drug Target*. 2(2): 101-112 (1994).
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)Tc-Based Radiopharmaceutical," *Bioconjug. Chem.* 13(6): 1200-1210 (2002).
Leamon CP et al., "Synthesis and biological evaluation of EC72: a new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem.* 10(7): 2397-2414, (2002).
Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.
Lee, R. J. and Huang, L., "Folate-Targeted, Anionic Liposome-Entrapped Polylysine-Condensed DNA for Tumor Cell-Specific Gene Transfer," *J. Biol. Chem.* 271(14): 8481-8487 (1996).
Lee, R. J. and Low, P. S, "Delivery of liposomes into cultured KB cells via folate receptor-mediated endocytosis," *J. Biol. Chem.* 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pterolyglutamic Acid to Pteroic Acid by Bacterial Degradation," *Archives of Biochemistry*, 1948; vol. 19, pp. 311-316.
Levy, Carl C., et al. "The Enzymatic Hydrolysis of Methotrexate and Folic Acid", 1967, *The Journal of Biological Chemistry*, vol. 242, No. 12, pp. 2933-2938.
Lewis et al., "Receptor-mediated folate uptake is positively regulated by disruption of actin cytoskeleton," *Cancer Res.* 58(14): 2952-2956 (1998).
Li et al, "Targeted delivery of antisense oligodeoxynucleotides by LPDII," *J. Liposome Res.* 7(1): 63 (1997).
Liu et al., "Targeted Drug Delivery to Chemoresistant Cells: Folic Acid Derivat zation of FdUMP[10] Enhances Cytotoxicity Toward 5-FU-Resistant Human Colorectal Tumor Cells," *J. Org. Chem.* 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).
Low P.S. et al., "Folate Receptor-Targeted Drugs for Cancer and Inflammatory Diseases," *Adv Drug Deliv Rev*, 2004;56(8):1055-28.
Lu et al., "Folate-targeted enzyme prodrug cancer therapy utilizing penicillin-V amidase and a doxorubicin prodrug," *J. Drug Target*, 7(1): 43-53 (1999).
Lu, J. Y. and Low, P. S., "Folate targeting of haptens to cancer cell surfaces mediates immunotherapy of syngeneic murine tumors," *Cancer Immunol Immunother*, 51: 153-162 (2002).
Lu, J. Y. and Low, P. S., "Folate-mediated delivery of macromolecular anticancer therapeutic agents," *Adv. Drug Del Rev*, 2002; 54(5): 675-693.
Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).
Mack D.O. et al., "The Carboxylation Activity of Vitamin K Analogs with Substitutions at Position 2, 3, or 5," *Journal of Biological Chemistry*, 1979; vol. 254, pp. 2656-2664.
Mancuso A.J. et al., "Activated Dimethyl Sulfoxide: Useful Reagents for Synthesis," *Synthesis*, 1981, pp. 165-184.
March, Advanced Organic Chemistry, 1992, John Wiley & Sons, 4th Ed., pp. 362-363, 816, 885, 896.
Mathais et al., "Receptor-mediated targeting of 67Ga-deferoxamine-folate to folate-receptor-positive human KB tumor xenografts," *Nucl Med Biol*, 26(1): 23-25 (1999).
Mathais et al., "Synthesis of [(99m)Tc]DTPA-folate and its evaluation as a folate-receptor-targeted radiopharmaceutical," *Bioconjug Chem*, 11(2): 253-257 (2000).
Mathias et al., "Indium- 111-DTPA-Folate as a potential folate-receptor-targeted radiopharmaceutical," *J Nucl. Med*, 39(9): 1579-1585 (1998).

(56) References Cited

OTHER PUBLICATIONS

Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).
Mathias, C. J., "A kit formulation for preparation of [(111)In]In-DTPA-folate, a folate-receptor-targeted radiopharmaceutical," *Nucl. Med. Biol.*, 25(6): 585-587 (1998).
Matsui et al., "Studies on mitomycins. III. The synthesis and properties of mitomycin derivatives," *J Antibiot*, 21: 189-198 (1968).
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
U.S. Appl. No. 13/785,542, filed Mar. 5, 2013, Leamon et al.
McAlinden TP et al., "Synthesis and Biological Evaluation of a Fluorescent Analogue of Folic Acid," *Biochemistry*, 1991; 30: 5674-81.
McHugh M et al., "Demonstration of a High Affinity Folate Binder in Human Cell Membranes and Its Characterization in Cultured Human KB Cells," *J Biol Chem*, 1979; 254(22):11312-8.
Melani et al., "Targeting of interleukin 2 to human ovarian carcinoma by fusion with a single-chain Fv of antifolate receptor antibody," *Cancer Res.* 58(18): 4146-4154 (1998).
Melby, E.L. et al, "Entry of Protein Toxins in Polarized Epithelial Cells"; *Cancer Research*, 1993; 53: 1755-1760.
Mislick et al., "Transfection of folate-polylysine DNA complexes: evidence for lysosomal delivery," *Bioconjug. Chem.*, 6(5): 512-515 (1995).
Mock D.M. et al., "Urinary Biotin Analogs Increase in Humans During Chronic Supplementation: the Analogs are Biotin Metabolites," *Am J Physiol Endocrinol Metab*, 1997; 272: E83-E85.
Morshed et al., "Folate transport proteins mediate the bidirectional transport of 5-methyltetrahydrofolate in cultured human proximal tubule cells," *J. Nutr.*, 127(6): 1137-1147 (1997).
Nair et al., "Folate analogs altered in the C9-N10 bridge region. 14. 11-Oxahomofolic acid, a potential antitumor agent", *Journal of Medical Chemistry*, 23: 59-65 (1980).
U.S. Appl. No. 13/841,349, filed Mar. 15, 2013, Vlahov et al.
U.S. Appl. No. 13/837,539, filed Mar. 15, 2013, Vlahov et al.
U.S. Appl. No. 13/841,078, filed Mar. 15, 2013, Vlahov et al.
Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).
Nair et al., "Folate analogs altered in the C9-N10 bridge region: N10-tosylisohomofolic acid and N10-tosylisohomoaminopterin," *Journal of Medical Chemistry*, 21: 673-677 (1978).
Nair et al., "Folate analogs altered in the C9-N10 bridge region: 11-thiohomofolic acid," *Journal of Medical Chemistry*, 22: 850-855 (1979).
Nair et al., "Folate analogs. 20. Synthesis and antifolate activity of 1',2',3',4',5',6'-hexahydrohomofolic acid," *Journal of Medical Chemistry*, 26: 135-140 (1983).
Nair et al., "Folate analogs. 21. Synthesis and antifolate and antitumor activities of N10-(cyanomethyl)-5,8-dideazafolic acid," *Journal of Medical Chemistry*, 26: 605-607 (1983).
Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).
Nair et al., "Folate analogues altered in the C9-N10 bridge region. 10-Oxafolic acid and 10-oxaaminopterin," *Journal of Medical Chemistry*, 19: 825-829 (1976).
Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).
Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.
Nimmo-Smith R.H. et al., "Some Effects of 2-deaminopteroylglutamic Acid upon Bacterial Growth," *J. Gen. Microbial.*, 1953; 9: 536-544.
Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.
Nomura, Makoto et al., "Development of an Efficient Intermediate α-[2-(Trimethylsilyl)ethoxy]-2-N-[2-(trimethylsilyl)ethoxycarbonyl] folic Acid, for the Synthesis of Folate (γ)-Conjugates, and Its Application to the Synthesis of Folate-Nucleoside Congugates," *Journal of Organic Chemistry*, 2000, vol. 65, pp. 5016-5021.
Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.
Oatis et al., "Synthesis of quinazoline analogues of folic acid modified at position 10," *Journal of Medical Chemistry*, 20: 1393-1396 (1977).
Olsnes S. et al., "Immunotoxins-entry into cells and mechanisms of action," *Immunology Today*, 1989; vol. 10, No. 9, pp. 291-295.
Patrick et al., "Folate Receptors As Potential Therapeutic Targets in Choroid Plexus Tumors of Sv40 Transgenic Mice," *J. Neurooncol*,. 32(2): 111-123 (1997).
Patrick et al., "Intracerebral bispecific ligand-antibody conjugate increases survival of animals bearing endogenously arising brain tumors," *Int. J. Cancer*, 78(4): 470-79 (1998).
Peltier, Hillary M., et al., "The Total Synthesis of Tubulysin D," 2006, *J. Am. Chem. Soc.*, No. 128, pp. 16018-16019.
Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Prabhu V. et al., "Arabidopsis dihydropteroate synthase: general properties and inhibition by reaction product and sulfonamides," *Phytochem.*, 1997; 45(1): 23-27.
Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Punj, V. et al., "Effect of Vitamin D Analog (1 α Hydroxy D5) Immunoconjugated to Her-2 Antibody on Breast Cancer," *Int. J Cancer*, 2004; 108: 922-929.
Raghavan B et al., "Cytotoxic Simplified Tubulysin Analogues," *J. Med. Chem.*, 2008; 51(6), pp. 1530-1533.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res.*, 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

(56) References Cited

OTHER PUBLICATIONS

Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4. 3'-Ethyl- and 3'- isopropylfolic acids," *Journal of Medical Chemistry*, 17: 219-222 (1974).
Rose W.C., "Taxol-Based Combination Chemotherapy and Other in Vivo Preclinical Antitumor Studies," *J Natl Cancer Inst Monogr*, 1993, No. 15, pp. 47-53.
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Roy et al., "Targeting T cells against brain tumors with a bispecific ligand-antibody conjugate," *Int. J. Cancer* 76(5): 761-66 (1998).
Sadasivan et al., "The complete amino acid sequence of a human folate binding protein from KB cells determined from the cDNA," *J. Biol. Chem.*, 1989; 264: 5806-5811.
Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14,2007, 1 page.
Semb J. et al., "Pteroic Acid Derivatives. V. Pteroyl-α-glutamyl-α-glutamylglutamic Acid, Pteroyl-γ-glutamyl-α-aglutamylglutamic Acid, Pteroyl-α-glutamyl-γ-glutamylglutamic Acid,"*JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits *Plasmodium falciparum* Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins—Powerful Inhibitors of Tubulin Polymerization from Microbacteria", *Angew. Chem. Int. Ed.*, 2004, No. 43, pp. 4888-4892.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6- (trifluoromethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Toffoli et al., "Overexpression of folate binding protein in ovarian cancers," *Int. J Cancer* 74(2): 193-198 (1997).
Toraya T. et al., "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh A. et al., "Temperature-sensitive differential affinity of Trail for its receptors. DR5 is the highest affinity receptor," *J Biol Chem.* 2000; 275(30):23319-25.
Turek et al., "Endocytosis of folate-protein conjugates: ultrastructural localization in KB cells," *J. Cell Sci.* 106: 423-430 (1993).
Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB

(56) References Cited

OTHER PUBLICATIONS cells with liposomes conjugated to folate via polyethylene glycol," *Proc. Natl. Acad. Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine-folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate binding protein (mFBP) in human CCRF-CEM leukemia cells," *Proceedings of the American Association for Cancer Research*, 1991; 32:328.
Wiener et al., "Targeting dendrimer-chelates to tumors and tumor cells expressing the high-affinity folate receptor," *Invest. Radiol.* 32(12): 748-54 (1997).
Wu M. et al., "Clustering of GPI-anchored folate receptor independent of both cross-linking and association with caveolin," *J. Membr. Biol.* 159(2): 137-147 (1997).
Zimmer H. et al., "Potential anticancer agents V., Synthesis of folic acid and pteroic acid analogs derived of caffeine and theophylline,"*Arzneimittelforschung*, 1966, 16(4), pp. 541-545.
Zimmerman, J., "Folic acid transport in organ-cultured mucosa of human intestine. Evidence for distinct carriers," *Gastroenterol.* 99(4): 964-972 (1990).
Angier, R. B., et al., "Pteroic Acid Analogs Containing Arsenic," J. American Chem. Soc., vol. 76, 1954, pp. 902-904.
Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.
Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189.
Wikipedia, Derivative (Chemistry), http://en.wikipedia.org/wiki/Derivative_(chemistry), downloaded Dec. 16, 2009.
Wikipedia, Analog (Chemistry), http://en.wikipedia.org/wiki/Analog_(chemistry), downloaded Dec. 16, 2009.
Wikipedia, List of Purification Methods in Chemistry, http://en.wikipedia.org/wiki/List_of_purification_methods_in_chemistry, downloaded Dec. 16, 2009.
Wikipedia, Solution, http://en.wikipedia.org/wiki/Solution, downloaded Dec. 17, 2009.
Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.
Wikipedia, Conjugate, http://en.wikipedia.org/wiki/Conjugate, downloaded Dec. 17, 2009.
Wikipedia, Complex (Chemistry), http://en.wikipedia.org/wiki/Complex_(chemistry), downloaded Dec. 23, 2009.
Leamon Christopher P., "Aspects of Folate-Mediated Drug Delivery . . . Beyond Purdue" PowerPoint Presentation presented at Purdue University on May 4, 1999, (22 pages).
Achilefu et al. "A New Method for the Synthesis of Tri-tert-butyl Diethylenetriaminepentaacetic Acid Its Derivatives" *J. Org. Chem.* 2000; 65:1562-1565.
Carl et al. "A novel connector linkage applicable in prodrug design" J. Med. Chem. 1981;24(5):479-480.
Coney et al. "Cloning of a tumor-associated antigent: MOv18 and MOv19 antibodies recognize a folate-binding protein" Cancer Res. 1991;51(22):6125-32.
Crapatureanu et al. "Molecular necklaces. Cross-linking hemoglobin with reagents containing covalently attached ligands" Bioconjugate Chemistry, 1999;10(6):1058-67. Abstract Only.
Darnell, Ed. Molecular Cell Biology W. H. Freeman, San Francisco 1990;326-333.
DeNardo, Gerald. "When is Too Much Too Much and Yet Not Enough? Alas, a Plethora of Opportunities but Where's the Beef?" J. of Nuclear Medicine 2000; 41(3):470-3.
Dorwald, F. Z., "Side Reactions in Organic Synthesis: A Guide to Successful Synthesis Design," Wiley-VCH, Weinheim, 2005, p. ix of preface.
Forgac. "Structure and function of vacuolar class of ATP-driven pumps" Physiological Rev. 1989; 69(3) :765-795.
Garrett et al. "Synthesis and characterisation of polyamine-poly(ethylene glycol) constructs for DNA binding and gene delivery" Bioorganic & Medicinal Chemistry, 2000; 8(7):1779-1797. Abstract Only.
Henderson et al. "Mediated uptake of folate by a high-affinity binding protein in sublines of L1210 cells adapted to nanomolar concentrations of folate" J. Membrane Biol., 1988;101:247-258.
Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57. Abstract Only.
Jansen et al., "Identification of a Membrane-Associated Folate-Binding Protein in Human Leukemic CCRF-CEM Cells with Transport-Related Methotrexate Resistance"in Cancer Res., 1989, 49, 2455-2459.
Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.
Kutsky RJ. Handbook of Vitamins, Minerals, and Hormones, 2nd Edition. New York: Van Nostrand Reinhold: 1981;263-277.
Kamen et al., 1986, "Receptor-mediated folate accumulation is regulated by cellular folate content" Proc. Natl. Acad. Sci., U.S.A. 83, 5933-5987.
Ke et al. "Targeting the Tumor-Associated Folate Receptor with a I IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.
Kemp et al. "New Protective Groups for Peptide Synthesis-I The Bic Group Base and Solvent Lability of the 5 -B enzi soxazolymethyl eneoxycarbonyl amino function" Tet. Lett. 1975;52:4625-4628.
Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.
Lee et al. "Prolonged circulating lives of single-chain Fv proteins conjugated with polyethylene glycol: a comparison of conjugation chemistries and compounds" Bioconjugate Chemistry, 1999;10(6):973-81. Abstract Only.
Li et al. "Local concentration of folate binding protein GP38 in sections of human ovarian carcinoma by concentration of in vitro quantitative autoradiography." J. Nucl. Med. 1996; 37:665-672.
Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.
Mehvar R "Dextrans for targeted and sustained delivery of therapeutic and imaging agents" [Review] Journal of Controlled Release, 2000;69(1):1-25. Abstract Only.

(56) References Cited

OTHER PUBLICATIONS

Miotti et al., "Characterization of Human Ovarian Carcinoma-Associated Antigens Defined by Novel Monoclonal Antibodies with Tumor-Restricted Specificity" Int. J. Cancer, 1987;39:297-303.
Pastan et al, eds. "The Pathways of Endocytosis" Endocytosis, Plenum Press, New York 1985;1-40.
Peterson et al. "Enzymatic cleavage of peptide-linked radiolabels from immunoconjugates" Bioconjugate Chemistry, 1999;10(4):553-7. Abstract Only.
Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.
Pizzorno et al. "5,10-Dideazatetrahydrofolic acid (DDATHF) transport in CCRFCEM and MA104 cell lines." J. Biol, Chem., 1993; 268(2):247-258.
Rothenberg et al. "Further observations on the folate-binding factor in some leukemic cells" J. Clin. Invest. 1971; 50(3):719-726.
Selhub et al. "The folate binding protein of rat kidney. Purification, properties, and cellular distribution" J. Biol. Chem. 1984;259(10):6601-6606.
Selhub et al. "Renal folate adsorption and the kidney folate binding protein I. Urinary Clearance studies" Am. J Physiol. 252:F750-F756.
Selhub et al. "Renal folate adsorption and the kidney folate binding protein II. Microinfusion studies" Am. J. Physiol. 252:F757-F760.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9. Abstract Only.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94. Abstract Only.
Toffoli et al. "Expression of folate binding protein as a prognostic factor for response to platinum-containing chemotherapy and survival in human ovarian cancer" Int. J. Cancer (Pred. Oncol) 1998; 79:121-126.
Weitman et al. "Distribution of the folate receptor GP38 in normal and malignant cell lines and tissues" Cancer Res. 1992;52(12):3396-3401.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg 737 Mutant Mice", 2003, *Kidney International*, vol. 63, pp. 1220-1229.
Bukanov Nikolay, O. et al., "Long-Lasting Arrest of Murine Polycystic Kidney Disease With CDK Inhibitor Roscovitine", Dec. 14, 2006; *Nature*; vol. 444; pp. 949-952.
Hay, Nissim, et al., "Upstream and Downstream of mTOR", 2004, *Genes & Development*, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.
Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.
Piontek, Klaus B., et al. "A Functional Floxed Allele of *Pkd1* that Can Be Conditionally Inactivated In Vivo", *J. Am. Soc. Nephrol.* vol. 15, pp. 3035-3043.
Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS.* vol. 103, No. 14, pp. 5466-5471.
Ke Cy et al., "Folate-Receptor-Targeting of In-111 Using Pteroic Acid Conjugates of Benzyl-DTPA and Benzyl-DOTA," J. Nucl. Med., 2004; 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery," Molecular Pharmacology, 2004; 66:1406-1414.
Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Functional analog, http://en.wikipedia.org/wiki/Functional_analog, downloaded Apr. 7, 2009.
Wikipedia, Folic acid, http://en.wikipedia.org/wiki/Folic_acid, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Matulic-Adamic J et al., "An efficient synthesis of the ribozyme-folate conjugate," Tetrahedron Letters, 2002; 43(25):4439-4441.
Harrison JG et al., A convenient synthetic route to oligonucleotide conjugates,: Bioorganic & Medicinal Chemistry Letters, 1997; 7(8): 1041-1046.

(56) References Cited

OTHER PUBLICATIONS

Dyson G., May P. "The Chemistry of Synthetic Pharmaceutical Substances", translation from English M.:—"The World", 1964, pp. 12-19.

Mashkovskiy M.D. Drugs, Moscow, New wave, 2001, vol. I, p. 11.

Robert Laplanche, et al.,"Physiologically Based Pharmacokinetic (PBPK) Modeling of Everolimus (RAD001) in Rats Involving Non-Linear Tissue Uptake,"Journal of Pharmacokinetics and Pharmacodynamics, 2007, vol. 34, No. 3, 373-400.

Pathalk et al., Enzymic protecting group techniques in organic synthesis, Stereosel. Biocatal. 775-797 (2000).

Dube D et al., "Preparation and Tumor Cell Uptake of Poly(*N*-isopropylacrylamide) Folate Conjugates"; *Bioconjugate Chem*, 2002; 13: 685-692.

Evans et al., "Synthesis of biotin conjugates of the antifungal compound cymoxanil," *Pest Manag Sci*, 2002; 58: 392-396.

Rao et al., Journal of Medicinal Chemistry, 1985, 28:1079-1088.

Conrad et al, Journal of Medicinal Chemistry, 1979, 22(4): 391-400.

Golub, T.R., et al., "Molecular Classification of Cancer: Class Discovery and Class Prediction by Gene Expression Monitoring," Science, 1999, vol. 286, 531-537 (Oct. 15, 1999).

Speckamp, et al.; "New Developments in the Chemistry of N-Acyliminium Ions and Related Intermediates" Tetrahedron 2000 vol. 56(24) 3817-3856.

Angier et al., Science, 1946, 103: 667-669.

Wolf et al., Journal of the American Chemical Society, 1947, 69: 2753-2759.

Parker et al., "Folate receptor expression in carcinomas and normal tissues determined by a quantitative radioligand binding assay," Analytical Biochemistry, 2005; 335:284-293.

Na, Wang, and Kohn, "7-N-(Mercaptoalkylmitomycins: Implications of Cyclization for Drug Function," J Am Chem Soc 124:4666-77 (2002.

Putnam et al., "Polymer conjugates with anticancer activity", Advances in Polymer Science 1995, 122, 55-123.

Umemoto et al., "Molecular design of methotrexate-antibody conjugates for targeted cancer treatment", Journal of Bioactive and Compatible Polymers, 1992, 7(2), 191-219.

Sanderson et al., "In vivo drug-linker stability of an anti-CD30 dipeptide-linked auristatin immunoconjugate," *Clinical Cancer Research*, 2005; 11:843-852.

International Search Report for PCT/US08/54189, completed Aug. 22, 2008.

Wu et al., "Enhancing the enantioselectivity of *candida* lipase catalyzed ester hydrolysis via noncovalent enzyme modification," *Journal of American Chemical Society*, 1990; 112:1990-1995.

Patterson et al., "Expedient synthesis of N-Methyl tubulysin analogues with high cytotoxicity," *Journal of Organic Chemistry*, 2008; 73:4365-4369.

\* cited by examiner

IHC ANALYSIS OF FR EXPRESSION IN PKD TISSUES
HUMAN SPECIMENS: mAb343

IHC ANALYSIS OF FR EXPRESSION IN PKD TISSUES
MURINE SPECIMENS: PU-17

16h INCUBATION WITH TEST ARTICLES

US 8,765,096 B2

METHODS AND COMPOSITIONS FOR TREATING AND DIAGNOSING KIDNEY DISEASE

CROSS-REFERENCE TO RELATED APPLICATIONS

This application is a continuation of U.S. application Ser. No. 12/527,316, filed Dec. 2, 2009, which is a U.S. national countpart application of international application serial no. PCT/US2008/054189, filed Feb. 16, 2008, under 35 USC §371, which claims priority to U.S. Provisional Patent Application Ser. No. 60/901,778, filed on Feb. 16, 2007, the entire disclosures of all of which are hereby incorporated by reference.

FIELD OF THE INVENTION

This invention relates to methods and compositions for treating and diagnosing kidney disease states. More particularly, ligands that bind to receptors overexpressed on proximal tubule cells are complexed with a diagnostic marker for use in diagnosis or to an antigen, a cytotoxin, or a cell growth inhibitor for use in the treatment of kidney disease states.

BACKGROUND

Diseases affecting kidney function are prevalent. For example, polycystic kidney disease (PKD) is a prevalent inherited disease. Adult PKD is an autosomal dominant disorder affecting approximately 600,000 people in the United States and 12.5 million world-wide. Infants can also present with autosomal recessive PKD which is rapidly developing and which can lead to renal insufficiency in the neonate. PKD and other kidney disease states (e.g., Dent's disease and nephrocytinosis) affect and manifest abnormal growth of kidney proximal tubule cells. PKD results in the proliferation of kidney epithelial cells and the formation of PKD renal cysts. The kidneys can become enlarged and symptoms including pain, bleeding, and kidney stones can occur. Associated problems include liver cysts, abdominal aneurysm, intracranial aneurysm, and renal insufficiency. It has been suggested that cellular processes associated with signal transduction, transcriptional regulation, and cell-cycle control are involved in cyst formation in PKD.

The folate receptor is a 38 KD GPI-anchored protein that binds the vitamin folic acid with high affinity (<1 nM). Following receptor binding, rapid endocytosis delivers a substantial fraction of the vitamins into the cell, where they are unloaded in an endosomal compartment at low pH. Importantly, covalent conjugation of small molecules, proteins, and even liposomes to folic acid does not block the vitamin's ability to bind the folate receptor, and therefore, folate-drug conjugates can readily be delivered to and can enter cells by receptor-mediated endocytosis. Because most cells use an unrelated reduced folate carrier to acquire the necessary folic acid, expression of the folate receptor is restricted to a few cell types, and normal tissues typically express low or nondetectable levels of the folate receptor. Folate receptors are overexpressed in proximal tubule cells.

The invention is based on the manifestation of abnormal proliferation of kidney proximal tubule cells in PKD and other kidney disease states that exhibit abnormal proximal tubule cell proliferation. These kidney disease states can be treated with ligands that bind to receptors overexpressed on proximal tubule cells wherein the ligands are complexed with an antigen, a cytotoxin, or a cell growth inhibitor for use in the treatment of the kidney disease states. These kidney disease states, including PKD, can also be diagnosed by using ligands that bind to receptors overexpressed on proximal tubule cells wherein the ligands are complexed with a diagnostic marker.

SUMMARY

In one embodiment, a method for diagnosing a kidney disease state is provided. The method comprises the steps of administering to a patient a composition comprising a conjugate or complex of the general formula V-L-D, where the group V comprises a vitamin receptor binding ligand that binds to kidney cells and the group D comprises a diagnostic marker, and diagnosing the kidney disease state.

In another embodiment, V comprises a folate receptor binding ligand or V comprises a folate receptor binding antibody or antibody fragment. In yet another embodiment, the marker can comprise a metal chelating moiety, or a fluorescent chromophore. In another illustrative embodiment, the disease state is selected from the group consisting of polycystic kidney disease, Dent's disease, nephrocytinosis, and Heymann nephritis.

In another embodiment, a method for treating a kidney disease state is provided. The method comprises the steps of administering to a patient suffering from the disease state an effective amount of a composition comprising a conjugate or complex of the general formula V-L-D where the group V comprises a vitamin receptor binding ligand that binds to kidney cells and the group D comprises an antigen, a cytotoxin, or a cell growth inhibitor, and eliminating the disease state.

In another embodiment, V comprises a folate receptor binding ligand or an antibody or antibody fragment that binds to the folate receptor. In another illustrative aspect, group D comprises an antigen, a cytotoxin, or a cell growth inhibitor. In yet another embodiment, the cell growth inhibitor is selected from the group consisting of epidermal growth factor receptor kinase inhibitors, inhibitors of the mTOR pathway, DNA alkylators, microtubule inhibitors, cell cycle inhibitors, and protein synthesis inhibitors. In another embodiment, the disease state is selected from the group consisting of polycystic kidney disease, Dent's disease, nephrocytinosis, and Heymann nephritis.

DETAILED DESCRIPTION

Figure 1:
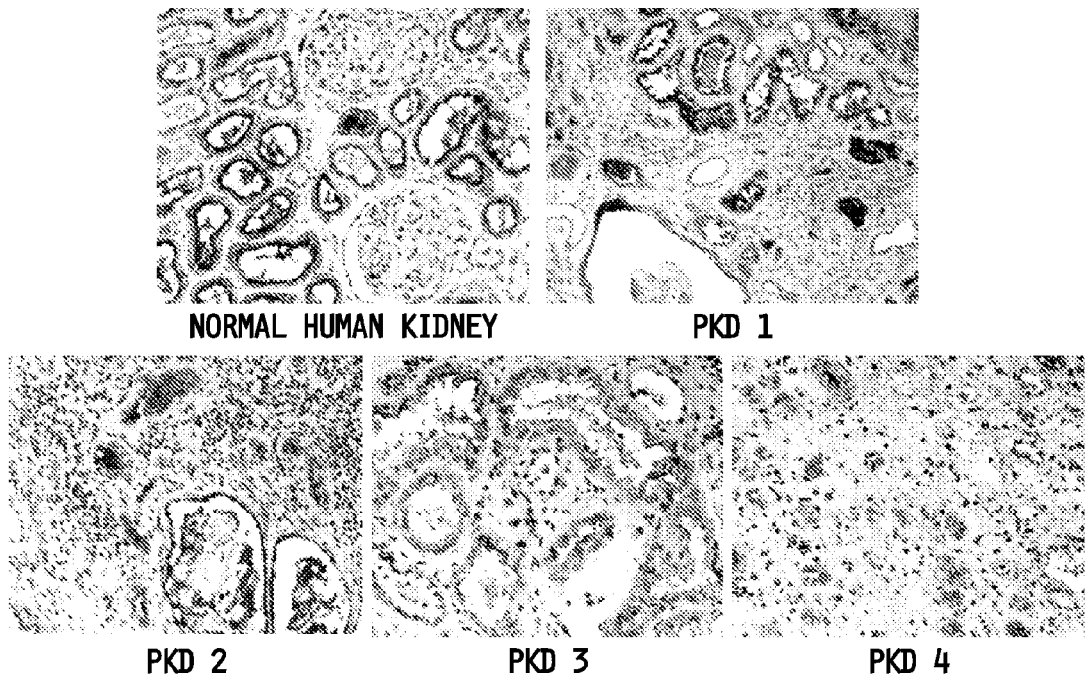
FIG. 1 shows IHC analysis of folate receptor expression in polycystic kidney disease tissues using a monoclonal antibody directed to the folate receptor for staining. The upper left panel shows normal human kidney tissue and the remainder of the panels show staining of cysts in polycystic kidney disease tissues using the anti-folate receptor monoclonal antibody.

Methods are provided for treating and diagnosing kidney disease states. Exemplary disease states include PKD, Dent's disease, nephrocytinosis, Heymann nephritis, and other diseases manifested by abnormal proliferation of proximal tubule cells of the kidney. PKD's can include, but are not limited to, autosomal dominant (adult) polycystic kidney disease and autosomal recessive (childhood) polycystic kidney disease. These disease states are characterized by abnormal proliferation of kidney proximal tubule cells. Such disease states can be diagnosed by contacting kidney proximal tubule cells with a composition comprising a conjugate of the general formula V-L-D wherein the group V comprises a ligand that binds to the kidney proximal tubule cells, and the group D comprises a diagnostic marker, and diagnosing the disease state. Such disease states can be treated by contacting kidney proximal tubule cells with a composition comprising a conjugate of the general formula V-L-D wherein the group V comprises a ligand that binds to the kidney proximal tubule cells, and the group D comprises an antigen, a cytotoxin, or a cell growth inhibitor, and eliminating the disease state.

As used herein, the terms "eliminated" and "eliminating" in reference to the disease state, mean reducing the symptoms or eliminating the symptoms of the disease state or preventing the progression or the reoccurrence of disease.

As used herein, the term "elimination" of the proximal tubule cell population causing the disease state that expresses the ligand receptor means that this cell population is killed or is completely or partially removed or inactivated which reduces the pathogenic characteristics of the disease state being treated.

The kidney disease states characterized by abnormal proliferation of proximal tubule cells can be treated in accordance with the methods disclosed herein by administering an effective amount of a composition V-L-D wherein V comprises a ligand that binds to proximal tubule cells and wherein the group D comprises an antigen, a cytotoxin, or a cell growth inhibitor. Such targeting conjugates, when administered to a patient suffering from a kidney disease state manifested by abnormal proximal tubule cell proliferation, work to concentrate and associate the conjugated cytotoxin, antigen, or cell growth inhibitor with the population of proximal tubule cells to kill the cells or alter cell function. The conjugate is typically administered parenterally, but can be delivered by any suitable method of administration (e.g., orally), as a composition comprising the conjugate and a pharmaceutically acceptable carrier therefore. Conjugate administration is typically continued until symptoms of the disease state are reduced or eliminated, or administration is continued after this time to prevent progression or reappearance of the disease.

For diagnosis the typical method of administration of the conjugates is parenteral administration, but any suitable method can be used. In this embodiment, kidney disease states can be diagnosed by administering parenterally to a patient a composition comprising a conjugate or complex of the general formula V-L-D where the group V comprises a ligand that binds to proximal tubule cells and the group D comprises a diagnostic marker, and diagnosing the disease state.

In one embodiment, for example, the diagnostic marker (e.g., a reporter molecule) can comprise a radiolabeled compound such as a chelating moiety and an element that is a radionuclide, for example a metal cation that is a radionuclide. In another embodiment, the radionuclide is selected from the group consisting of technetium, gallium, indium, and a positron emitting radionuclide (PET imaging agent). In another embodiment, the diagnostic marker can comprise a fluorescent chromophore such as, for example, fluorescein, rhodamine, Texas Red, phycoerythrin, Oregon Green, AlexaFluor 488 (Molecular Probes, Eugene, Oreg.), Cy3, Cy5, Cy7, and the like. Imaging agents are described in U.S. Pat. No. 7,128,893 and in U.S. Patent Publ. No. 20070009434, each incorporated herein by reference.

Diagnosis typically occurs before treatment. However, in the diagnostic methods described herein, the term "diagnosis" can also mean monitoring of the disease state before, during, or after treatment to determine the progression of the disease state. The monitoring can occur before, during, or after treatment, or combinations thereof, to determine the efficacy of therapy, or to predict future episodes of disease. The diagnostic method can be any suitable method known in the art, including imaging methods, such as intravital imaging.

The method disclosed herein can be used for both human clinical medicine and veterinary applications. Thus, the patient or animal afflicted with the kidney disease state and in need of diagnosis or therapy can be a human, or in the case of veterinary applications, can be a laboratory, agricultural, domestic or wild animal. In embodiments where the conjugates are administered to the patient or animal, the conjugates can be administered parenterally to the animal or patient suffering from the kidney disease state, for example, intradermally, subcutaneously, intramuscularly, intraperitoneally, or intravenously. Alternatively, the conjugates can be administered to the animal or patient by other medically useful procedures and effective doses can be administered in standard or prolonged release dosage forms, such as a slow pump.

The therapeutic method described herein can be used alone or in combination with other therapeutic methods recognized for the treatment of kidney disease states.

In the ligand conjugates of the general formula V-L-D, the group V is a ligand that binds to proximal tubule cells when the conjugates are used to diagnose or treat kidney disease states. Any of a wide number of binding ligands can be employed. Acceptable ligands include, for example, folate receptor binding ligands, and analogs thereof, and antibodies or antibody fragments capable of recognizing and binding to surface moieties expressed on proximal tubule cells, in particular when these cells proliferate abnormally. In one embodiment, the binding ligand is folic acid, a folic acid analog, or another folate receptor binding molecule. In another embodiment the binding ligand is a specific monoclonal or polyclonal antibody or an Fab or an scFv (i.e., a single chain variable region) fragment of an antibody capable of binding to receptors overexpressed on proximal tubule cells, for example, when these cells proliferate abnormally.

In one embodiment, the binding ligand can be folic acid, a folic acid analog, or another folate receptor-binding molecule. Analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroyl-glutamic acid (dichloromethotrexate).

In another embodiment, other vitamins can be used as the binding ligand. The vitamins that can be used in accordance with the methods described herein include niacin, pantothenic acid, folic acid, riboflavin, thiamine, biotin, vitamin $B_{12}$, vitamins A, D, E and K, other related vitamin molecules, analogs and derivatives thereof, and combinations thereof.

In other embodiments, the binding ligand can be any ligand that binds to a receptor expressed or overexpressed on proximal tubule cells, in particular when they proliferate abnormally (e.g., EGF, KGF, or leptin). In another embodiment, the binding ligand can be any ligand that binds to a receptor expressed or overexpressed on proximal tubule cells proliferating abnormally and involved in a kidney disease state.

The targeted conjugates used for diagnosing or treating disease states mediated by proximal tubule cells proliferating abnormally have the formula V-L-D, wherein V is a ligand capable of binding to the proximal tubule cells, and the group D comprises a diagnostic marker or an antigen (such as an immunogen), cytotoxin, or a cell growth inhibitor. In such conjugates wherein the group V is folic acid, a folic acid analog, or another folic acid receptor binding ligand, these conjugates are described in detail in U.S. Pat. No. 5,688,488, the specification of which is incorporated herein by reference. That patent, as well as related U.S. Pat. Nos. 5,416,016 and 5,108,921, and related U.S. patent application Ser. No. 10/765,336, each incorporated herein by reference, describe methods and examples for preparing conjugates useful in accordance with the methods described herein. The present targeted diagnostic and therapeutic agents can be prepared and used following general protocols described in those earlier patents and patent applications, and by the protocols described herein.

In accordance with another embodiment, there is provided a method of treating kidney disease states by administering to a patient suffering from such disease state an effective amount of a composition comprising a conjugate of the general formula V-L-D wherein V is as defined above and the group D comprises a cytotoxin, an antigen (i.e., a compound administered to a patient for the purpose of eliciting an immune response in vivo), or a cell growth inhibitor. The group V can be any of the ligands described above. Exemplary of cytotoxic moieties useful for forming conjugates for use in accordance with the methods described herein include art-recognized chemotherapeutic agents such as antimetabolites, methotrexate, busulfan, carboplatin, chlorambucil, cisplatin and other platinum compounds, plant alkaloids, hydroxyurea, teniposide, and bleomycin, MEK kinase inhibitors, MAP kinase pathway inhibitors, PI-3-kinase inhibitors, NFκB pathway inhibitors, pro-apoptotic agents, apoptosis-inducing agents, proteins such as pokeweed, saporin, momordin, and gelonin, didemnin B, verrucarin A, geldanamycin, toxins, and the like. Such cytotoxic compounds can be directly conjugated to the targeting ligand, for example, folate or another folate receptor-binding ligand, or they can be formulated in liposomes or other small particles which themselves can be targeted to proximal tubule cells by pendent targeting ligands V non-covalently or covalently linked to one or more liposome components.

In another embodiment, the group D comprises a cell growth inhibitor, and the inhibitor can be covalently linked to the targeting ligand V, for example, a folate receptor-binding ligand or a proximal tubule cell-binding antibody or antibody fragment (i.e., an antibody to a receptor overexpressed on proximal tubule cells that are proliferating abnormally). The ligand can be linked directly, or the ligand can be encapsulated in a liposome which is itself targeted to the proximal tubule cells by pendent targeting ligands V covalently or non-covalently linked to one or more liposome components. Cell growth inhibitors can be selected from the group consisting of epidermal growth factor receptor kinase inhibitors and other kinase inhibitors (e.g. rapamycin and other inhibitors of the mTOR pathway, r-roscovitine and other cyclin-dependent kinase inhibitors), DNA alkylators (e.g., nitrogen mustards (e.g., cyclophosphamide), ethyleneamines, alkyl sulfonates, nitrosoureas, and triazene derivatives), microtubule inhibitors (e.g., tamoxiphen, paclitaxel, docetaxel (and other taxols), vincristine, vinblastine, colcemid, and colchicine), cell cycle inhibitors (e.g., cytosine arabinoside, purine analogs, and pyrimidine analogs), and protein synthesis inhibitors (e.g., proteosome inhibitors). In one embodiment, rapamycin (RAPAMUNE®, Wyeth Pharmaceuticals, Inc., Madison, N.J.) is the cell growth inhibitor. Rapamycin is described in Shillingford, et al., *PNAS* 103: 5466-5471 (2006), incorporated herein by reference. In another embodiment, more than one of these drugs can be conjugated to a ligand, such as folate, to form, for example, a dual-drug conjugate.

In another embodiment, conjugates V-L-D where D is an antigen or a cell growth inhibitor can be administered in combination with a cytotoxic compound. The cytotoxic compounds listed above are among the compounds suitable for this purpose.

In one embodiment, conjugates are described herein, and such conjugates may be used in the treatment methods described herein. Illustratively, the conjugates have the general formula

V-L-D where V is a folate receptor binding ligand, L is an optional linker, and D is a cell-growth inhibitor, an antigen, or a cytotoxin.

In one embodiment, the folate receptor binding ligand is folate or an analog of folate, or alternatively a derivative of either folate or an analog thereof. As used herein, the term "folate" or "folates" may refer to folate itself, or such analogs and derivatives of folate. However, it is to be understood that other folate receptor binding ligands in addition to folates are contemplated herein. Illustratively, such folate receptor binding ligands include any compound capable or specific or selective binding to folate receptors, especially those receptors present on the surface of cells.

In another embodiment, the optional linker is absent, and the conjugate is formed by directly attaching the folate receptor binding ligand to the cell-growth inhibitor, a cytotoxin, or an antigen. In another embodiment, the optional linker is present and is a divalent chemical fragment comprising a chain of carbon, nitrogen, oxygen, silicon, sulfur, and phosphorus. It is to be understood that the foregoing atoms may be arranged in any chemically meaningful way. In one variation, peroxide bonds, i.e. —O—O— do not form part of the linker. Generally, the linker is formed from the foregoing atoms by arranging those atoms to form functional groups, including but not limited to, alkylene, cycloalkylene, arylene, ether, amino, hydroxylamino, oximino, hydrazine, hydrazono, thio, disulfide, carbonyl, carboxyl, carbamoyl, thiocarbonyl, thiocarboxyl, thiocarbamoyl, xanthyl, silyl, phosphinyl, phosphonyl, phosphate, and like groups that may be linked together to construct the linker. It is appreciated that each of these fragments may also be independently substituted.

In another embodiment, the drug is a cell-growth inhibitor. Illustrative of such cell-growth inhibitors are epidermal growth factor (EGF) receptor kinase inhibitors. Further illustrative of such cell-growth inhibitor are DNA alkylators, microtubule inhibitors, cell cycle inhibitors, and protein synthesis inhibitors.

In another illustrative embodiment, such cell growth inhibitors are compounds that inhibit the mammalian target of rapamycin, also referred to as mTOR. mTOR is a serine/threonine protein kinase that has been reported to regulate cell growth, cell proliferation, cell motility, cell survival, protein synthesis, and transcription (see generally, Beevers et al. "Curcumin inhibits the mammalian target of rapamycin-mediated signaling pathways in cancer cells," *International Journal of Cancer*, 119(4):757-64 (2006); Hay & Sonenberg N "Upstream and downstream of mTOR," *Genes & Development*, 18(16): 1926-45 (2004)). mTOR has been shown to function as the catalytic subunit of two distinct molecular complexes in cells. mTOR Complex 1 (mTORC1) is composed of mTOR, regulatory associated protein of mTOR (Raptor), and mammalian LST8/G-protein β-subunit like protein (mLST8/GβL). This complex possesses the classic features of mTOR by functioning as a nutrient/energy/redox sensor and controlling protein synthesis. mTOR Complex 2 (mTORC2) is composed of mTOR, rapamycin-insensitive companion of mTOR (Rictor), GβL, and mammalian stress-activated protein kinase interacting protein 1 (mSIN1). mTORC2 has been shown to function as an important regulator of the cytoskeleton through its stimulation of F-actin stress fibers, paxillin, RhoA, Rac1, Cdc42, and protein kinase C α (PKCα). In addition, mTORC2 has also been reported to be a "PDK2."

Illustrative of such mTOR inhibitors is rapamycin, and analogs and derivatives of rapamycin, such as are described in U.S. Pat. No. 7,153,957 (Regioselective synthesis of CCI-779), U.S. Pat. No. 7,122,361 (Compositions employing a novel human kinase), U.S. Pat. No. 7,105,328 (Methods for screening for compounds that modulate pd-1 signaling), U.S. Pat. No. 7,074,804 (CCI-779 Isomer C), U.S. Pat. No. 7,060,797 (Composition and method for treating lupus nephritis), U.S. Pat. No. 7,060,709 (Method of treating hepatic fibrosis), U.S. Pat. No. 7,029,674 (Methods for downmodulating immune cells using an antibody to PD-1), U.S. Pat. No. 7,019,014 (Process for producing anticancer agent LL-D45042), U.S. Pat. No. 6,958,153 (Skin penetration enhancing components), U.S. Pat. No. 6,821,731 (Expression analysis of FKBP nucleic acids and polypeptides useful in the diagnosis of prostate cancer), U.S. Pat. No. 6,713,607 (Effector proteins of Rapamycin), U.S. Pat. No. 6,680,330 (Rapamycin dialdehydes), U.S. Pat. No. 6,677,357 (Rapamycin 29-enols), U.S. Pat. No. 6,670,355 (Method of treating cardiovascular disease), U.S. Pat. No. 6,617,333 (Antineoplastic combinations), U.S. Pat. No. 6,541,612 (Monoclonal antibodies obtained using rapamycin position 27 conjugates as an immunogen), U.S. Pat. No. 6,511,986 (Method of treating estrogen receptor positive carcinoma), U.S. Pat. No. 6,440,991 (Ethers of 7-desmethlrapamycin), U.S. Pat. No. 6,432,973 (Water soluble rapamycin esters), U.S. Pat. No. 6,399,626 (Hydroxyesters of 7-desmethylrapamycin), and U.S. Pat. No. 6,399,625 (1-oxorapamycins), each incorporated herein by reference.

In another illustrative embodiment, the linker includes an amino acid or a peptide from 2 to about 20 amino acids in length. As used herein, it is to be understood that amino acids are illustratively selected from the naturally occurring amino acids, or stereoisomers thereof. In addition, amino acids may be non-naturally occurring, and have for example the general formula:

—N(R)—(CR'R")$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. It is further appreciated that water solubilizing amino acids may be included in the linker to facilitate uptake and transport of the conjugates described herein. For example, the amino acids may be selected from asparagine, aspartic acid, cysteine, glutamic acid, lysine, glutamine, arginine, serine, ornitine, threonine, and the like.

In another illustrative embodiment, the bivalent linker (L) comprises one or more spacer linkers, heteroatom linkers, and releasable (i.e., cleavable) linkers, and combinations thereof, in any order. The term "releasable linker" as used herein generally refers to a linker that includes at least one bond that can be broken under physiological conditions (e.g., a pH-labile, acid-labile, oxidatively-labile, enzyme-labile bond, and the like). It is appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

It is also understood that a cleavable bond can connect two adjacent atoms within the releasable linker and/or connect other linkers or V and/or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an heteroatom linker, a spacer linker, another releasable linker, the drug, or analog or derivative thereof, or the vitamin, or analog or derivative thereof, following breakage of the bond, the releasable linker is separated from the other moiety.

The lability of the cleavable bond can be adjusted by, for example, substitutional changes at or near the cleavable bond, such as including alpha branching adjacent to a cleavable disulfide bond, increasing the hydrophobicity of substituents on silicon in a moiety having silicon-oxygen bond that may be hydrolyzed, homologating alkoxy groups that form part of a ketal or acetal that may be hydrolyzed, and the like.

In one embodiment, the present invention provides a vitamin receptor binding drug delivery conjugate. The drug delivery conjugate consists of a vitamin receptor binding moiety, bivalent linker (L), and a drug. The vitamin receptor binding moiety is a vitamin, or an analog or a derivative thereof, capable of binding to vitamin receptors, and the drug (antigen, cytotoxin, or cell growth inhibitor) includes analogs or derivatives thereof exhibiting drug activity. The vitamin, or the analog or the derivative thereof, is covalently attached to the bivalent linker (L), and the drug, or the analog or the derivative thereof, is also covalently attached to the bivalent linker (L). The bivalent linker (L) comprises one or more spacer linkers, releasable linkers, and heteroatom linkers, and combinations thereof, in any order. For example, the heteroatom linker can be nitrogen, and the releasable linker and the heteroatom linker can be taken together to form a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below. Alternatively, the heteroatom linkers can be nitrogen, oxygen, sulfur, and the formulae —(NHR$^1$NHR$^2$)—, —SO—, —(SO$_2$)—, and —N(R$^3$)O—, wherein R$^1$, R$^2$, and R$^3$ are each independently selected from hydrogen, alkyl, aryl, arylalkyl, substituted aryl, substituted arylalkyl, heteroaryl, substituted heteroaryl, and alkoxyalkyl. In another embodiment, the heteroatom linker can be oxygen, the spacer linker can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the heteroatom linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$, as defined below. In this embodiment, the heteroatom linker can be nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the heteroatom linker can be sulfur, and the spacer linkers can be alkylene and cycloalkylene, wherein each of the spacer linkers is optionally substituted with carboxy, and the spacer linker is bonded to the sulfur to form a thiol. In another embodiment, the heteroatom linker can be sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the heteroatom linker can be nitrogen, and the releasable linker and the heteroatom linker can be taken together to form a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^1$ and the heteroatom linker can be taken together with the spacer linker to which they are bound to form an heterocycle.

The releasable linkers can be methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the heteroatom linker can be oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the heteroatom linker can be oxygen, and the releasable linker can be methylene, wherein the methylene is substituted with an optionally-substituted aryl, and the releasable linker is bonded to the oxygen to form an acetal or ketal. Further, the heteroatom linker can be oxygen, and the releasable linker can be sulfonylalkyl, and the releasable linker is bonded to the oxygen to form an alkylsulfonate.

In another embodiment of the above releasable linker embodiment, the heteroatom linker can be nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the heteroatom linker can be oxygen, and the releasable linkers can be alkylene(dialkylsilyl), alkylene (alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the heteroatom linker can be nitrogen, and the releasable linkers can be carbonylarylcarbonyl, carbonyl(carboxyaryl)carbonyl, carbonyl(biscarboxyaryl) carbonyl, and the releasable linker can be bonded to the heteroatom nitrogen to form an amide, and also bonded to the drug nitrogen to form an amide.

In the above releasable linker embodiment, the drug can include an oxygen atom, the heteroatom linker can be nitrogen, and the releasable linkers can be carbonylarylcarbonyl, carbonyl(carboxyaryl)carbonyl, carbonyl(biscarboxyaryl) carbonyl, and the releasable linker can be bonded to the heteroatom linker nitrogen to form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^2$ and the heteroatom linker can be taken together with the releasable linker to which they are bound to form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

The drug can include a nitrogen atom, and the releasable linker can be haloalkylenecarbonyl, optionally substituted with a substituent $X^2$, and the releasable linker is bonded to the drug nitrogen to form an amide.

The drug can include an oxygen atom, and the releasable linker can be haloalkylenecarbonyl, optionally substituted with a substituent $X^2$, and the releasable linker is bonded to the drug oxygen to form an ester.

The drug can include a double-bonded nitrogen atom, and in this embodiment, the releasable linkers can be alkylenecarbonylamino and 1-(alkylenecarbonylamino) succinimid-3-yl, and the releasable linker can be bonded to the drug nitrogen to form an hydrazone.

The drug can include a sulfur atom, and in this embodiment, the releasable linkers can be alkylenethio and carbonylalkylthio, and the releasable linker can be bonded to the drug sulfur to form a disulfide.

The term "aryl" as used herein refers to an aromatic mono or polycyclic ring of carbon atoms, such as phenyl, naphthyl, and the like.

The term "heteroaryl" as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein refers to aryl or heteroaryl substituted with one or more substituents selected, such as halo, hydroxy, amino, alkyl or dialkylamino, alkoxy, alkylsulfonyl, cyano, nitro, and the like.

In addition, the following linkers are contemplated. It is understood that these linkers may be combined with each other and other space, heteroatom and releaseable linkers to prepare the conjugates described herein. Illustrative linkers, and combinations of spacer and heteroatom linkers include:

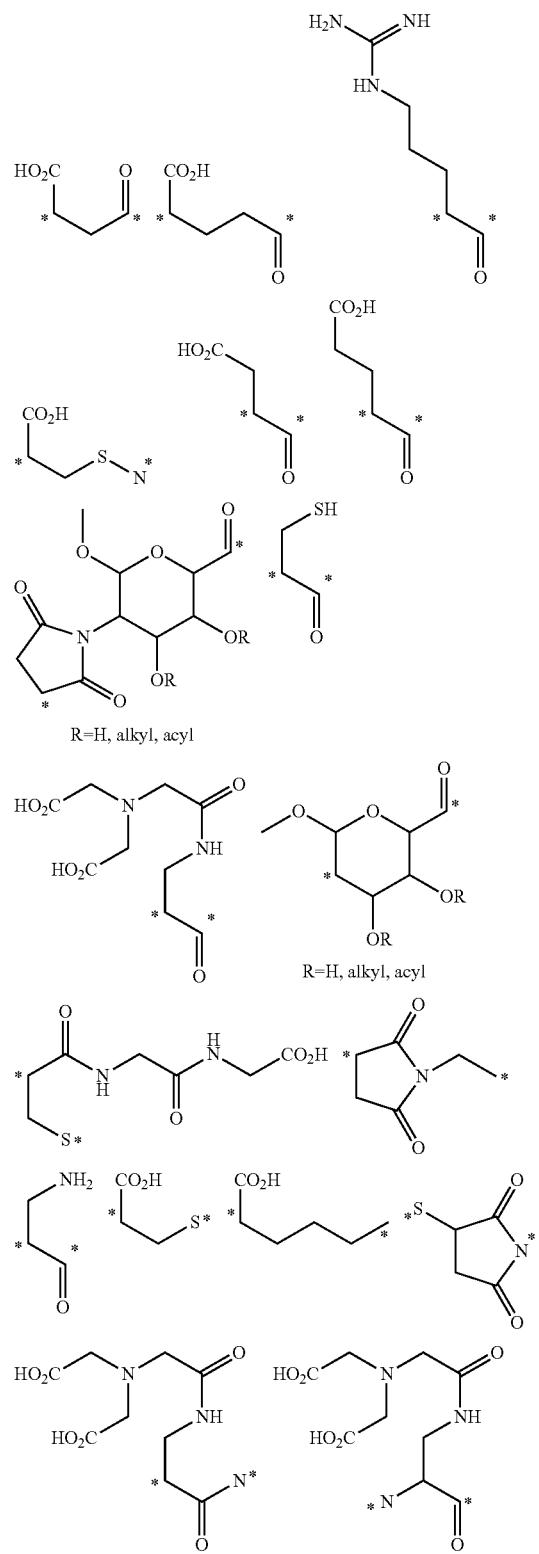

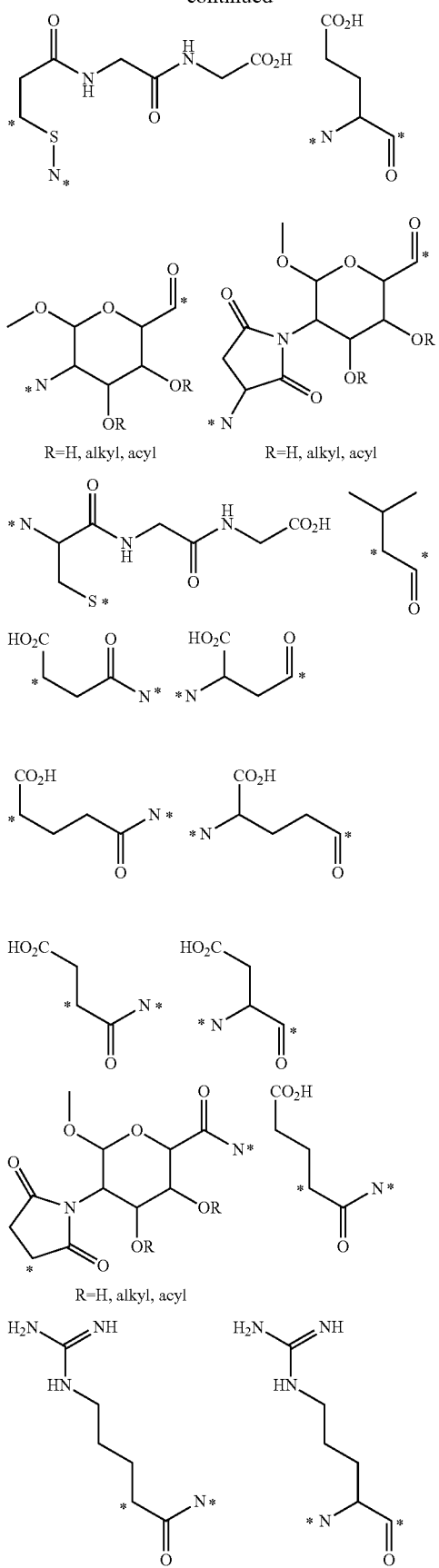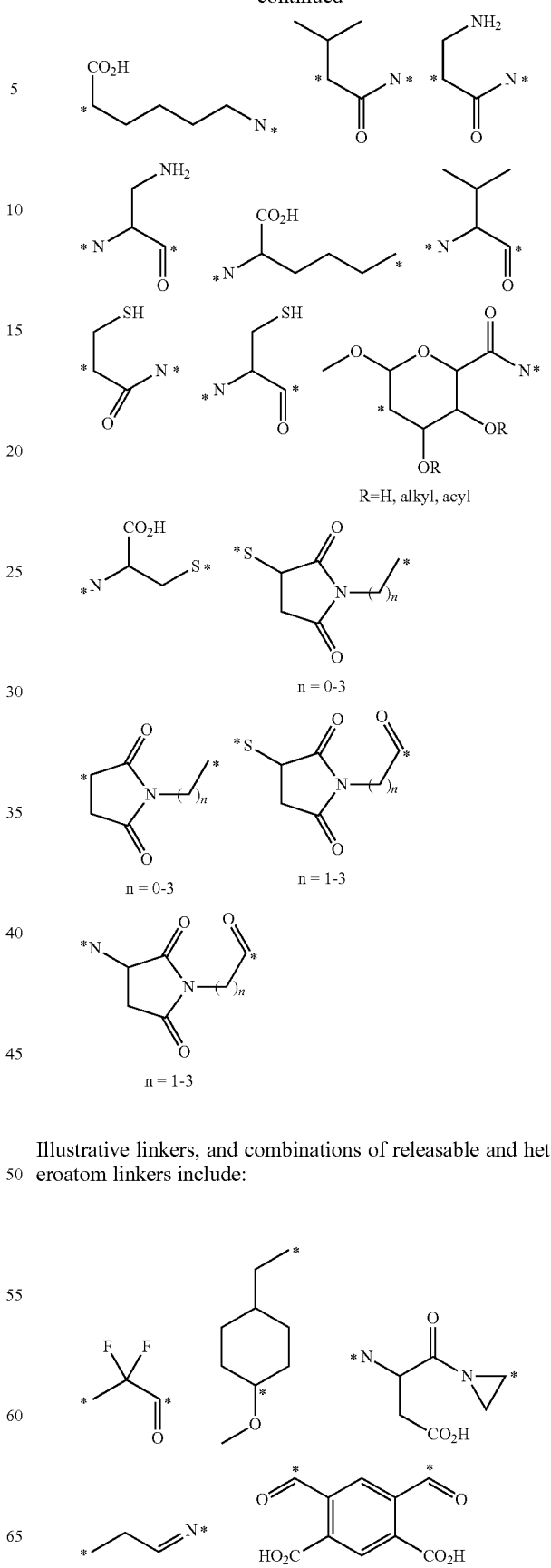
Illustrative linkers, and combinations of releasable and heteroatom linkers include:

Illustrative folate receptor binding ligands include folic acid, folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folates useful as complex forming ligands for this invention are the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3′,5′-dichloro-4-amino-4-deoxy-$N^{10}$-methylpteroylglutamic acid (dichloromethotrexate). The foregoing folic acid analogs and/or derivatives are conventionally termed "folate" or "folates," reflecting their ability to bind with folate-receptors, and such ligands when conjugated with exogenous molecules are effective to enhance transmembrane transport, such as via folate-mediated endocytosis as described herein. Other suitable ligands capable of binding to folate receptors to initiate receptor-mediated endocytotic transport of the complex include anti-idiotypic antibodies to the folate receptor. An exogenous molecule in complex with an anti-idiotypic antibody to a folate receptor is used to trigger transmembrane transport of the complex in accordance with the present invention.

Generally, any manner of forming a conjugate between the bivalent linker (L) and the folate receptor-binding ligand, or between the bivalent linker (L) and the cell-growth inhibitor, antigen, or cytotoxin, or analog or derivative thereof, including any intervening heteroatom linkers, may be used. The conjugate may be formed by direct conjugation of any of these molecules, for example, through hydrogen, ionic, or covalent bonds. Covalent bonding can occur, for example, through the formation of amide, ester, disulfide, or imino bonds between acid, aldehyde, hydroxy, amino, sulfhydryl, hydrazo, and like groups, such as those described herein.

The spacer and/or releasable linker (i.e., cleavable linker) can be any biocompatible linker. The cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. Generally, the spacer and/or releasable linker comprises about 1 to about 50 atoms in length, more typically about 2 to about 20 carbon atoms. It is appreciated that lower molecular weight linkers (i.e., those having an approximate molecular weight of about 30 to about 300) may be employed. Precursors to such linkers are selected to have suitably reactive groups at the points of attachment, such as nucleophilic or electrophilic functional groups, or both, optionally in a protected form with a readily cleavable protecting group to facilitate their use in synthesis of the intermediate species.

In another illustrative embodiment, the conjugate is a compound of the following formula:

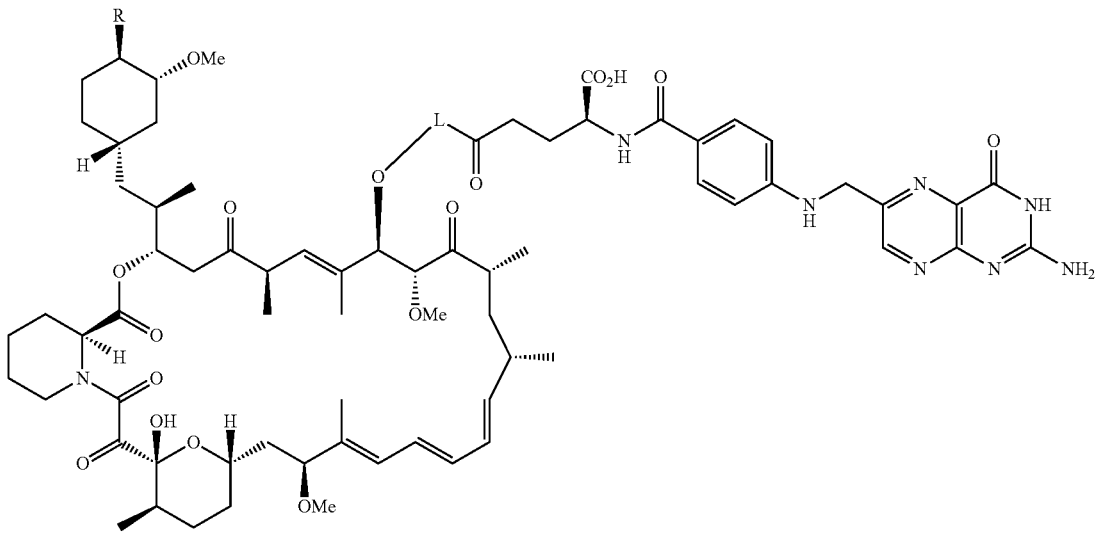

wherein:

R is —O—C=O.CR$^7$R$^8$R$^9$;

R$^7$ is hydrogen, alkyl of 1-6 carbon atoms, alkenyl of 2-7 carbon atoms, alkynyl of 2-7 carbon atoms, —(CR$^{12}$R$^{13}$)$_f$OR$^{10}$, —CF$_3$, —F, or —CO$_2$R$^{10}$;

R$^{10}$ is hydrogen, alkyl of 1-6 carbon atoms, alkenyl of 2-7 carbon atoms, alkynyl of 2-7 carbon atoms, triphenylmethyl, benzyl, alkoxymethyl of 2-7 carbon atoms, chloroethyl, or tetrahydropyranyl; R$^8$ and R$^9$ are taken together to form X;

X is 2-phenyl-1,3,2-dioxaborinan-5-yl or 2-phenyl-1,3,2-dioxaborinan-4-yl, wherein the phenyl may be optionally substituted;

R$^{12}$ and R$^{13}$ are each, independently, hydrogen, alkyl of 1-6 carbon atoms, alkenyl of 2-7 carbon atoms, alkynyl of 2-7 carbon atoms, trifluoromethyl, or —F;

f=0-6; and

L is as defined herein.

In another illustrative embodiment, the conjugate is a compound of the following formula:

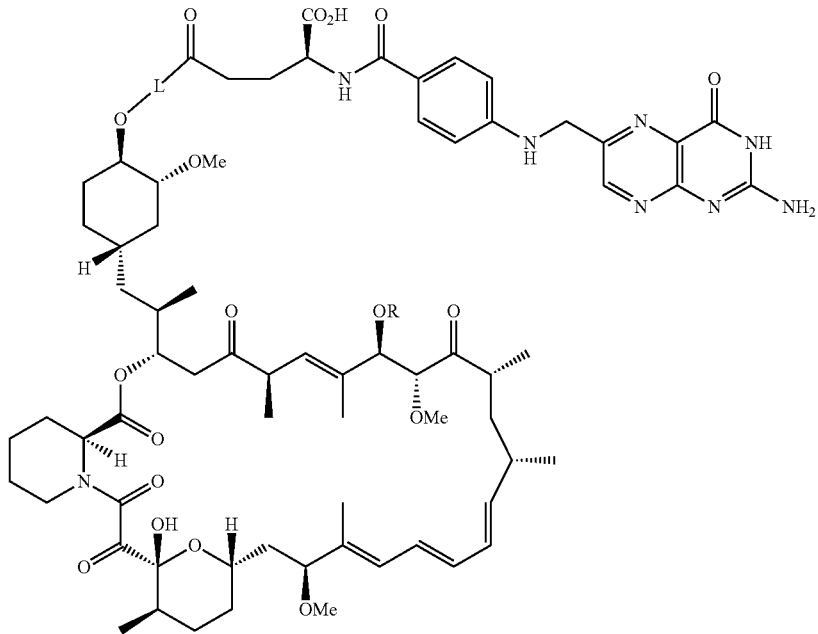

wherein R in each instance is the same or different and is independently selected from the group consisting of alkyl of 1-6 carbon atoms, phenyl and benzyl; and L is as defined herein.

In another illustrative embodiment, the conjugate is a compound of the following formula:

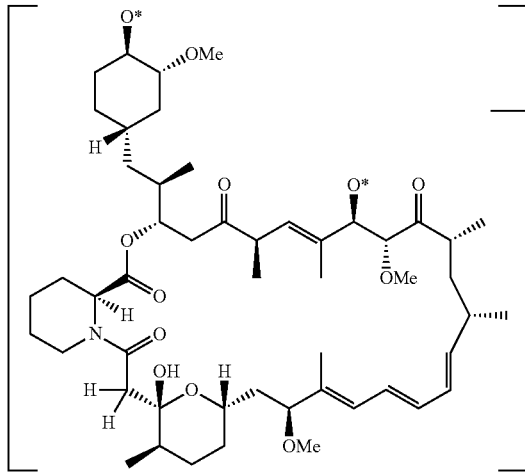
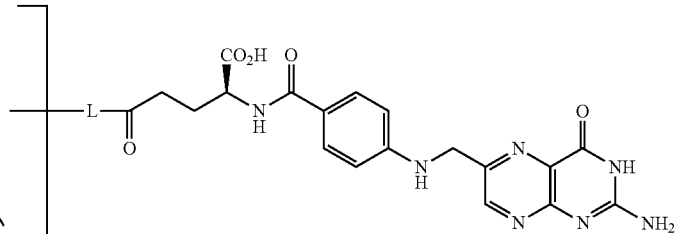

where L is as defined herein, and L is connected to the rapamycin or analog or derivative thereof at either of (O*), and the other of (O*) is substituted with R, wherein R is hydrogen or —(R$^a$—W—R$^b$)$_n$—;
W is a linking group;
R$^a$ is selected from the group consisting of carbonyl, —S(O)—, —S(O)$_2$—, —P(O)$_2$—, —P(O)(CH$_3$)—, —C(S)—, and —CH$_2$C(O)—;
R$^b$ is a selected from the group consisting of carbonyl, —NH—, —S—, —CH$_2$—, and —O—; and
n=1-5.

In another illustrative embodiment, the conjugate is a compound of the following formula:

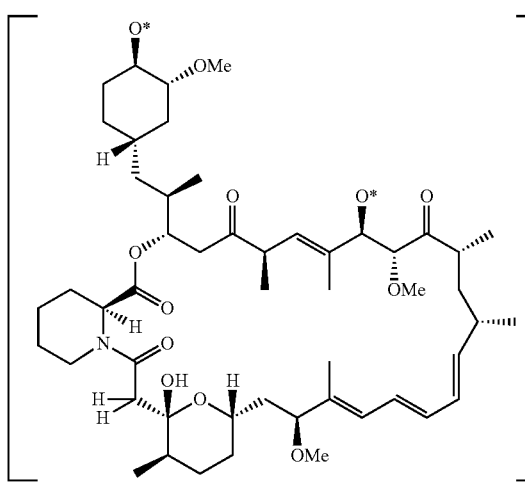
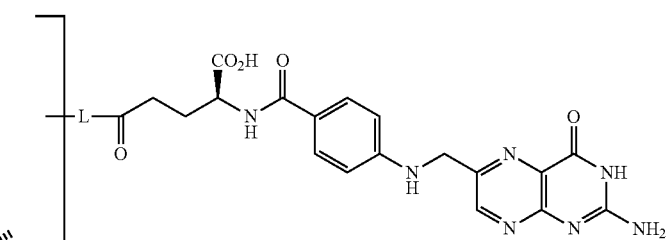

where L is as defined herein, and L is connected to the rapamycin or analog or derivative thereof at either of (O*), and the other of (O*) is substituted with R, wherein R is hydrogen, thioalkyl of 1-6 carbon atoms, arylalkyl of 7-10 carbon atoms, hydroxyalkyl of 1-6 carbon atoms, dihydroxyalkyl of 1-6 carbon atoms, alkoxyalkyl of 2-12 carbon atoms, hydroxyalkoxyalkyl of 2-12 carbon atoms, acyloxyalkyl of 3-12 carbon atoms, aminoalkyl of 1-6 carbon atoms, alkylaminoalkyl of 1-6 carbon atoms per alkyl group, dialkylaminoalkyl of 1-6 carbon atoms per alkyl group, alkoxycarbonylaminoalkyl of 3-12 carbon atoms, acylaminoalkyl of 3-12 carbon atoms, alkenyl of 2-7 carbon atoms, arylsulfamidoalkyl having 1-6 carbon atoms in the alkyl group, hydroxyalkylallyl of 4-9 carbon atoms, dihydroxyalkylallyl of 4-9 carbon atoms, or dioxolanylallyl.

In another illustrative embodiment, the conjugate is a compound of the following formula:

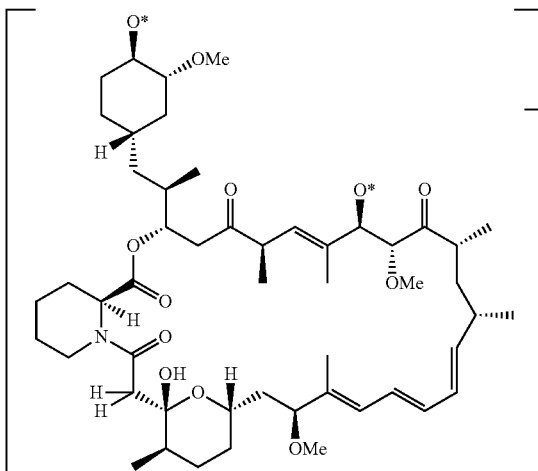

where L is as defined herein, and L is connected to the rapamycin or analog or derivative thereof at either of (O*), and the other of (O*) is substituted with R, wherein R is hydrogen or —CO(CR³R⁴)$_b$(CR⁵R⁶)$_d$CR⁷R⁸R⁹; where R³ and R⁴ are each, independently, hydrogen, alkyl of 1-6 carbon atoms, alkenyl of 2-7 carbon atoms, alkynyl of 2-7 carbon atoms, trifluoromethyl, or F; R⁵ and R⁶ are each, independently, hydrogen, alkyl of 1-6 carbon atoms, alkenyl of 2-7 carbon atoms, alkynyl of 2-7 carbon atoms, (CR³R⁴)$_f$OR¹⁰, CF₃, F, or CO₂R¹¹; R⁷ is hydrogen, alkyl of 1-6 carbon atoms, alkenyl of 2-7 carbon atoms, alkynyl of 2-7 carbon atoms, (CR³R⁴)$_f$OR¹⁰, CF₃, F, or CO₂R¹¹;

R⁸ and R⁹ are each, independently, hydrogen, alkyl of 1-6 carbon atoms, alkenyl of 2-7 carbon atoms, alkynyl of 2-7 carbon atoms, (CR³R⁴)$_f$OR¹⁰, CF₃, F, or CO₂R¹¹;

R¹⁰ is hydrogen or COCH₂SCH₂CH₂(OCH₂CH₂)$_n$OCH₃;
R¹¹ is hydrogen, alkyl of 1-6 carbon atoms, alkenyl of 2-7 carbon atoms, alkynyl of 2-7 carbon atoms, or phenylalkyl of 7-10 carbon atoms;
b=0-6; d=0-6; f=0-6; and n=5-450.

In another illustrative embodiment, the conjugate is a compound of the following formula:

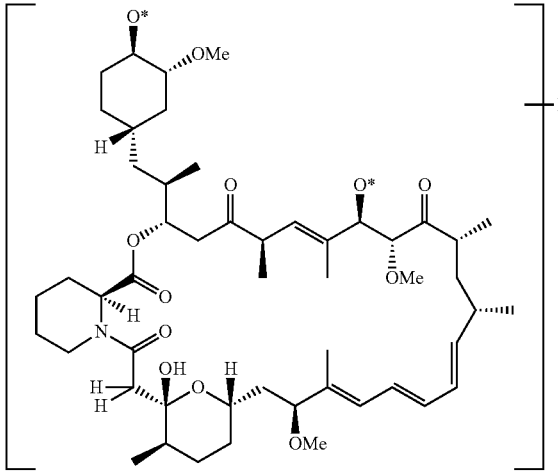

where L is as defined herein, and L is connected to the rapamycin or analog or derivative thereof at either of (O*),

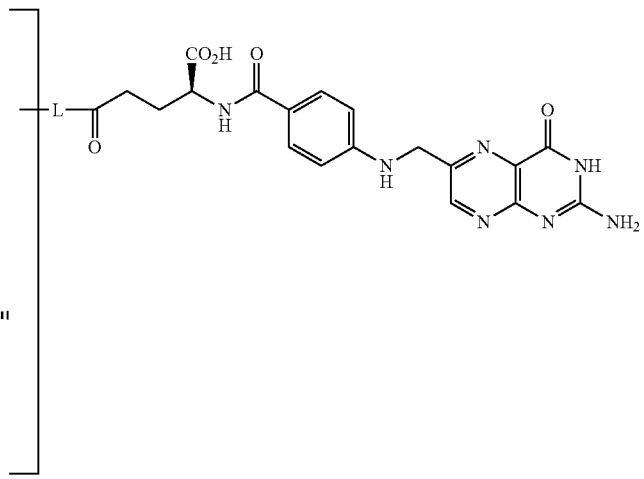

and the other of (O*) is substituted with R, wherein R is hydrogen or —CO(CR³R⁴)$_b$(CR⁵R⁶)$_d$CR⁷R⁸R⁹; where R³ and R⁴ are each, independently, hydrogen, alkyl of 1-6 carbon atoms, alkenyl of 2-7 carbon atoms, alkynyl of 2-7 carbon atoms, trifluoromethyl, or F;

R⁵ and R⁶ are each, independently, hydrogen, alkyl of 1-6 carbon atoms, alkenyl of 2-7 carbon atoms, alkynyl of 2-7 carbon atoms, (CR³R⁴)$_f$OH, CF₃, F, or CO₂R¹¹;

R⁷ is hydrogen, alkyl of 1-6 carbon atoms, alkenyl of 2-7 carbon atoms, alkynyl of 2-7 carbon atoms, (CR³R⁴)$_f$OH, CF₃, F, or CO₂R¹¹;

R⁸ and R⁹ are each, independently, hydrogen, alkyl of 1-6 carbon atoms, alkenyl of 2-7 carbon atoms, alkynyl of 2-7 carbon atoms, (CR³R⁴)$_f$OH, CF₃, F, or CO₂R¹¹;

R¹¹ is hydrogen, alkyl of 1-6 carbon atoms, alkenyl of 2-7 carbon atoms, alkynyl of 2-7 carbon atoms, or phenylalkyl of 7-10 carbon atoms;
b=0-6; d=0-6; and f=0-6.

In one aspect of each of the foregoing, L includes an amino acid or a peptide. In another aspect of each of the foregoing, L includes amino acids selected from cysteine, aspartic acid, glutamic acid, arginine, and lysine. It is to be understood that either enantiomer of such amino acids may be included in such illustrative linkers in each instance. In another aspect of each of the foregoing, L includes a releasable linker. In one variation, the releasable linker comprises a disulfide bond. In another variation, the releasable linker comprises a carbonate.

In another illustrative embodiment, the conjugate is a compound of the following formula:

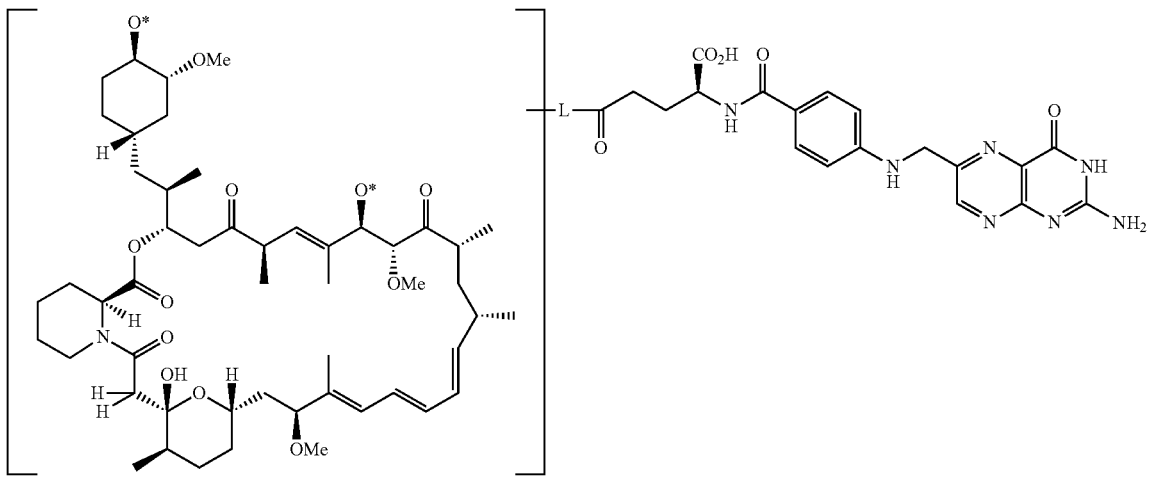

where L is as defined herein, and L is connected to the rapamycin or analog or derivative thereof at either of (O*). In one aspect, L includes an amino acid or a peptide. In another aspect, L includes amino acids selected from cysteine, aspartic acid, glutamic acid, arginine, and lysine. It is to be understood that either enantiomer of such amino acids may be included in such illustrative linkers in each instance. In another aspect, L includes a releasable linker. In one variation, the releasable linker comprises a disulfide bond. In another variation, the releasable linker comprises a carbonate.

In another illustrative embodiment, the conjugate is a compound of the following formula:

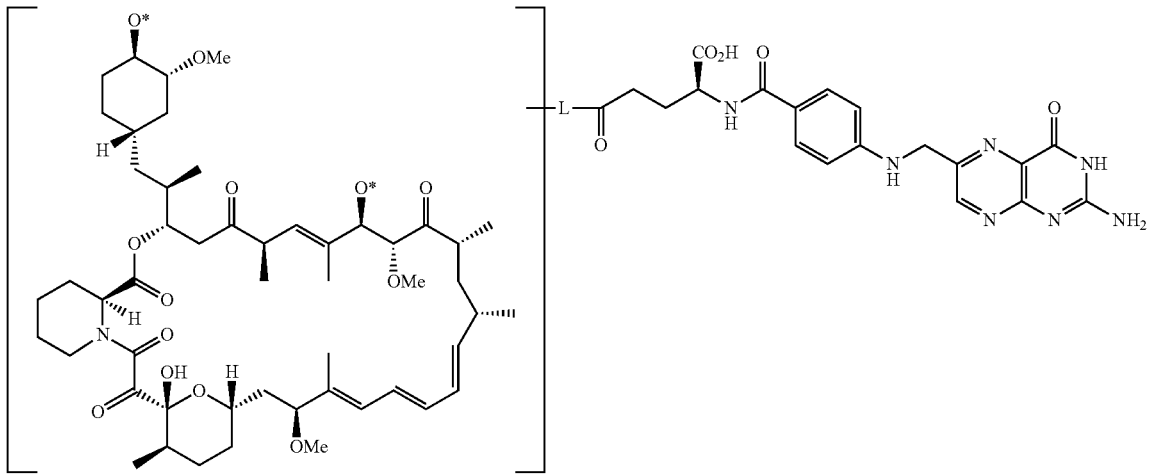

where L is as defined herein, and L is connected to the rapamycin or analog or derivative thereof at either of (O*). In one aspect, L includes an amino acid or a peptide. In another aspect, L includes amino acids selected from cysteine, aspartic acid, glutamic acid, arginine, and lysine. It is to be understood that either enantiomer of such amino acids may be included in such illustrative linkers in each instance. In another aspect, L includes a releasable linker. In one variation, the releasable linker comprises a disulfide bond. In another variation, the releasable linker comprises a carbonate.

In another illustrative embodiment, the conjugate is a compound of the following formula:

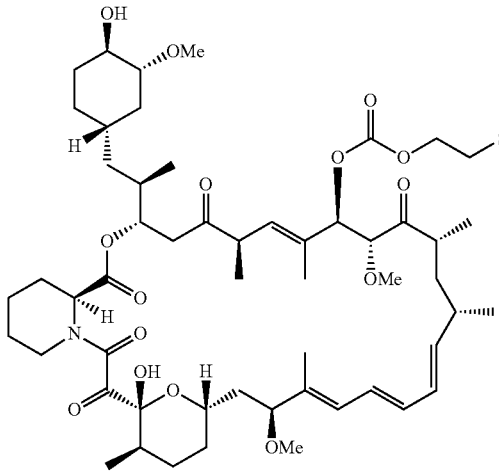
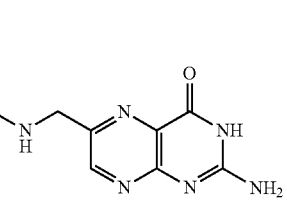

where L is as defined herein. In one aspect, L includes an amino acid or a peptide. In another aspect, L includes amino acids selected from cysteine, aspartic acid, glutamic acid, arginine, and lysine. It is to be understood that either enantiomer of such amino acids may be included in such illustrative linkers in each instance.

Figure 3:
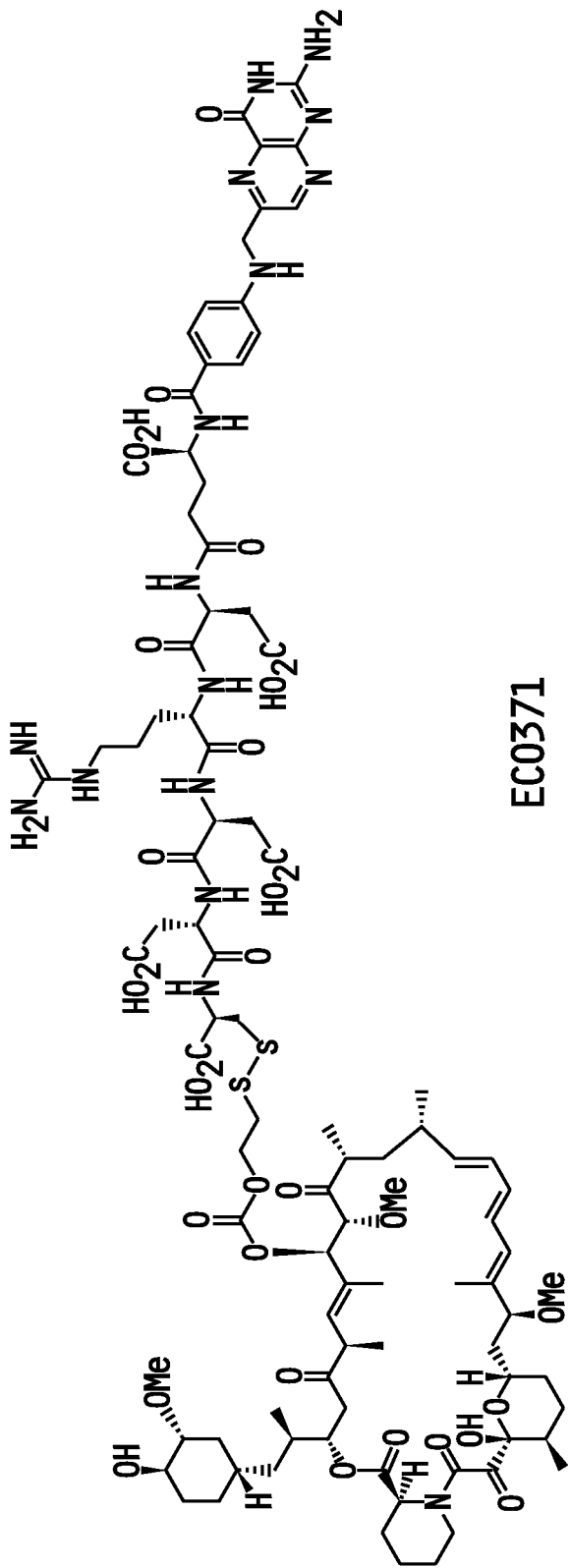
FIG. 3 shows the structure of EC0371, a folate-rapamycin conjugate.

In another illustrative embodiment, the conjugate is a compound of the following formula (EC0371; see also FIG. 3):

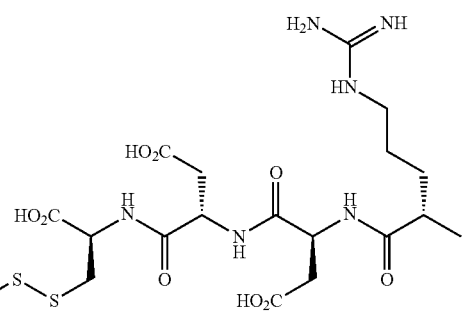
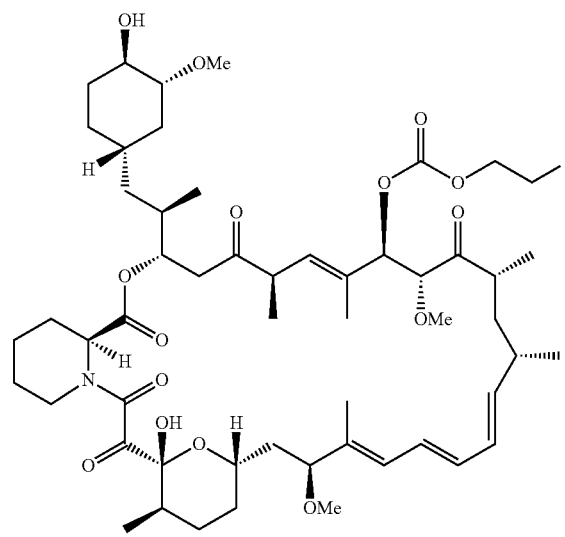

-continued

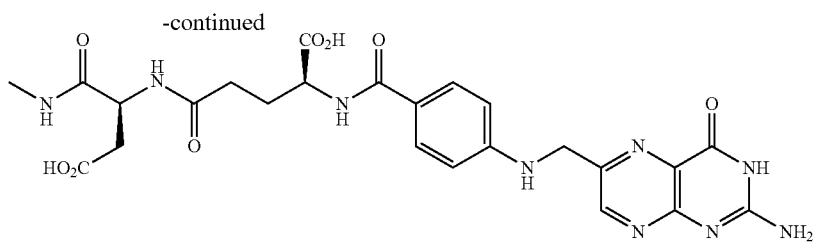

The compounds described herein may be prepared by general organic synthetic reactions, such as those described in U.S. patent application Ser. No. 10/765,336, the disclosure of which is incorporated herein by reference.

Briefly, the following chemical transformations are described for preparing the compounds described herein.

General amide and ester formation. For example, where the heteroatom linker is a nitrogen atom, and the terminal functional group present on the spacer linker or the releasable linker is a carbonyl group, the required amide group can be obtained by coupling reactions or acylation reactions of the corresponding carboxylic acid or derivative, where L is a suitably-selected leaving group such as halo, triflate, pentafluorophenoxy, trimethylsilyloxy, succinimide-N-oxy, and the like, and an amine, as illustrated in Scheme 1.

Scheme 1

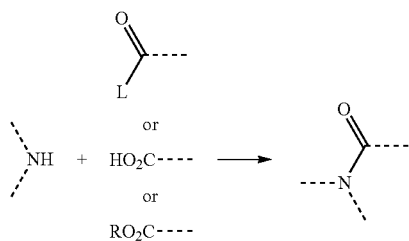

Coupling reagents include DCC, EDC, RRDQ, CGI, HBTU, TBTU, HOBT/DCC, HOBT/EDC, BOP-Cl, PyBOP, PyBroP, and the like. Alternatively, the parent acid can be converted into an activated carbonyl derivative, such as an acid chloride, a N-hydroxysuccinimidyl ester, a pentafluorophenyl ester, and the like. The amide-forming reaction can also be conducted in the presence of a base, such as triethylamine, diisopropylethylamine, N,N-dimethyl-4-aminopyridine, and the like. Suitable solvents for forming amides described herein include $CH_2Cl_2$, $CHCl_3$, THF, DMF, DMSO, acetonitrile, EtOAc, and the like. Illustratively, the amides can be prepared at temperatures in the range from about −15° C. to about 80° C., or from about 0° C. to about 45° C. Amides can be formed from, for example, nitrogen-containing aziridine rings, carbohydrates, and α-halogenated carboxylic acids. Illustrative carboxylic acid derivatives useful for forming amides include compounds having the formulae:

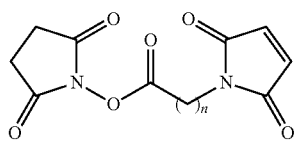

and the like, where n is an integer such as 1, 2, 3, or 4.

Similarly, where the heteroatom linker is an oxygen atom and the terminal functional group present on the spacer linker or the releasable linker is a carbonyl group, the required ester group can be obtained by coupling reactions of the corresponding carboxylic acid or derivative, and an alcohol.

Coupling reagents include DCC, EDC, CDI, BOP, PyBOP, isopropenyl chloroformate, EEDQ, DEAD, $PPh_3$, and the like. Solvents include $CH_2Cl_2$, $CHCl_3$, THF, DMF, DMSO, acetonitrile, EtOAc, and the like. Bases include triethylamine, diisopropyl-ethylamine, and N,N-dimethyl-4-aminopyridine. Alternatively, the parent acid can be converted into an activated carbonyl derivative, such as an acid chloride, a N-hydroxysuccinimidyl ester, a pentafluorophenyl ester, and the like.

General ketal and acetal formation. Furthermore, where the heteroatom linker is an oxygen atom, and the functional group present on the spacer linker or the releasable linker is 1-alkoxyalkyl, the required acetal or ketal group can be formed by ketal and acetal forming reactions of the corresponding alcohol and an enol ether, as illustrated in Scheme 2.

Scheme 2

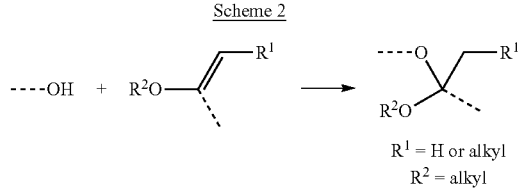

$R^1$ = H or alkyl
$R^2$ = alkyl

Solvents include alcohols, $CH_2Cl_2$, $CHCl_3$, THF, diethylether, DMF, DMSO, acetonitrile, EtOAc, and the like. The formation of such acetals and ketals can be accomplished with an acid catalyst. Where the heteroatom linker comprises two oxygen atoms, and the releasable linker is methylene, optionally substituted with a group $X^2$ as described herein, the required symmetrical acetal or ketal group can be illustratively formed by acetal and ketal forming reactions from the corresponding alcohols and an aldehyde or ketone, as illustrated in Scheme 3.

Scheme 3

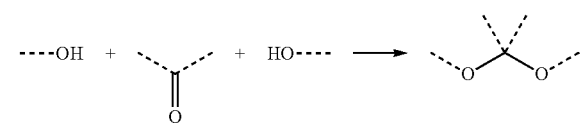

Alternatively, where the methylene is substituted with an optionally-substituted aryl group, the required acetal or ketal may be prepared stepwise, where L is a suitably selected leaving group such as halo, trifluoroacetoxy, triflate, and the like, as illustrated in Scheme 4. The process illustrated in Scheme 4 is a conventional preparation, and generally follows the procedure reviewed by R. R. Schmidt et al., *Chem. Rev.*, 2000, 100, 4423-42, the disclosure of which is incorporated herein by reference.

Scheme 4

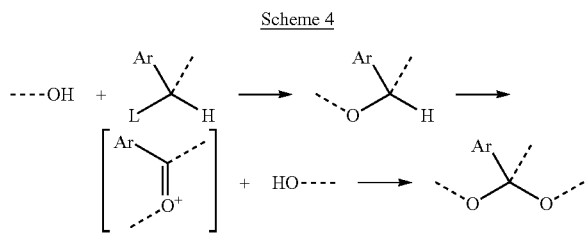

The resulting arylalkyl ether is treated with an oxidizing agent, such as DDQ, and the like, to generate an intermediate oxonium ion that is subsequently treated with another alcohol to generate the acetal or ketal.

General succinimide formation. Furthermore, where the heteroatom linker is, for example, a nitrogen, oxygen, or sulfur atom, and the functional group present on the spacer linker or the releasable linker is a succinimide derivative, the resulting carbon-heteroatom bond can be formed by a Michael addition of the corresponding amine, alcohol, or thiol, and a maleimide derivative, where X is the heteroatom linker, as illustrated in Scheme 5.

Scheme 5

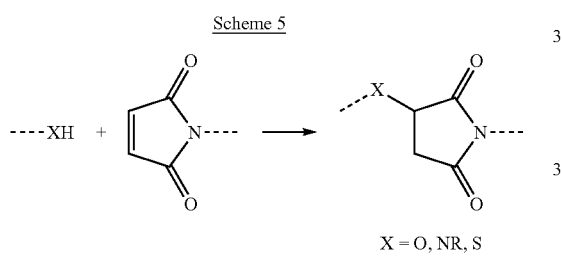

X = O, NR, S

Solvents for performing the Michael addition include THF, EtOAc, $CH_2Cl_2$, DMF, DMSO, $H_2O$ and the like. The formation of such Michael adducts can be accomplished with the addition of equimolar amounts of bases, such as triethylamine, Hünig's base or by adjusting the pH of water solutions to 6.0-7.4. It is appreciated that when the heteroatom linker is an oxygen or nitrogen atom, reaction conditions may be adjusted to facilitate the Michael addition, such as, for example, by using higher reaction temperatures, adding catalysts, using more polar solvents, such as DMF, DMSO, and the like, and activating the maleimide with silylating reagents.

General silyloxy formation. Furthermore, where the heteroatom linker is an oxygen atom, and the functional group present on the spacer linker or the releasable linker is a silyl derivative, the required silyloxy group may be formed by reacting the corresponding silyl derivative, and an alcohol, where L is a suitably selected leaving group such as halo, trifluoroacetoxy, triflate, and the like, as illustrated in Scheme 6.

Scheme 6

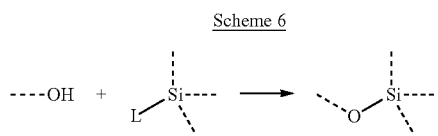

Silyl derivatives include properly functionalized silyl derivatives such as vinylsulfonoalkyl diaryl, or diaryl, or alkyl aryl silyl chloride. Instead of a vinylsulfonoalkyl group, a β-chloroethylsulfonoalkyl precursor may be used. Any aprotic and anhydrous solvent and any nitrogen-containing base may serve as a reaction medium. The temperature range employed in this transformation may vary between −78° C. and 80° C.

General hydrazone formation. Furthermore, where the heteroatom linker is a nitrogen atom, and the functional group present on the spacer linker or the releasable linker is an iminyl derivative, the required hydrazone group can be formed by reacting the corresponding aldehyde or ketone, and a hydrazine or acylhydrazine derivative, as illustrated in Scheme 7, equations (1) and (2) respectively.

Scheme 7

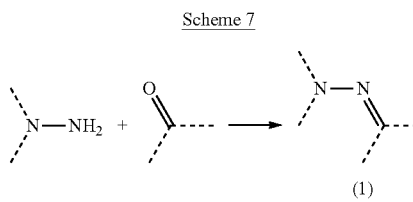

(1)

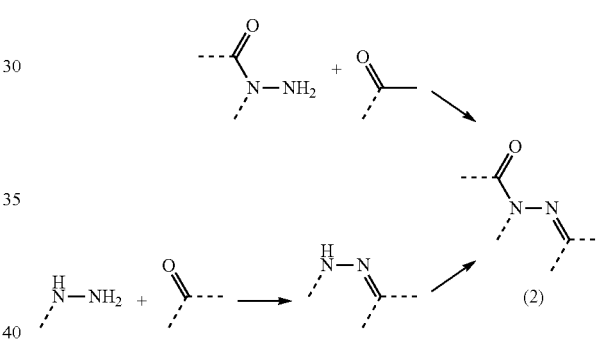

(2)

Solvents that can be used include THF, EtOAc, $CH_2Cl_2$, $CHCl_3$, $CCl_4$, DMF, DMSO, MeOH and the like. The temperature range employed in this transformation may vary between 0° C. and 80° C. Any acidic catalyst such as a mineral acid, $H_3CCOOH$, $F_3CCOOH$, p-TsOH·$H_2O$, pyridinium p-toluene sulfonate, and the like can be used. In the case of the acylhydrazone in equation (2), the acylhydrazone may be prepared by initially acylating hydrazine with a suitable carboxylic acid or derivative, as generally described above in Scheme 1, and subsequently reacting the acylhydrazide with the corresponding aldehyde or ketone to form the acylhydrazone. Alternatively, the hydrazone functionality may be initially formed by reacting hydrazine with the corresponding aldehyde or ketone. The resulting hydrazone may subsequently be acylated with a suitable carboxylic acid or derivative, as generally described above in Scheme 1.

General disulfide formation. Furthermore, where the heteroatom linker is a sulfur atom, and the functional group present on the releasable linker is an alkylenethiol derivative, the required disulfide group can be formed by reacting the corresponding alkyl or aryl sulfonylthioalkyl derivative, or the corresponding heteroaryldithioalkyl derivative such as a pyridin-2-yldithioalkyl derivative, and the like, with an alkylenethiol derivative, as illustrated in Scheme 8.

Scheme 8

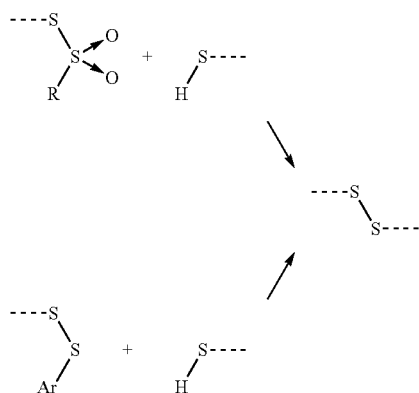

Solvents that can be used are THF, EtOAc, CH$_2$Cl$_2$, CHCl$_3$, CCl$_4$, DMF, DMSO, and the like. The temperature range employed in this transformation may vary between 0° C. and 80° C. The required alkyl or aryl sulfonylthioalkyl derivative may be prepared using art-recognized protocols, and also according to the method of Ranasinghe and Fuchs, *Synth. Commun.* 18(3), 227-32 (1988), the disclosure of which is incorporated herein by reference. Other methods of preparing unsymmetrical dialkyl disulfides are based on a transthiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference.

General carbonate formation. Furthermore, where the heteroatom linker is an oxygen atom, and the functional group present on the spacer linker or the releasable linker is an alkoxycarbonyl derivative, the required carbonate group can be formed by reacting the corresponding hydroxy-substituted compound with an activated alkoxycarbonyl derivative where L is a suitable leaving group, as illustrated in Scheme 9.

Scheme 9

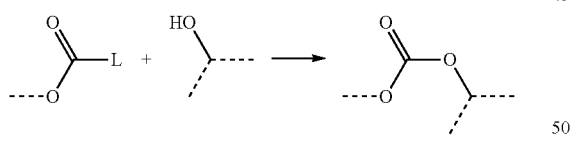

Solvents that can be used are THF, EtOAc, CH$_2$Cl$_2$, CHCl$_3$, CCl$_4$, DMF, DMSO, and the like. The temperature range employed in this transformation may vary between 0° C. and 80° C. Any basic catalyst such as an inorganic base, an amine base, a polymer bound base, and the like can be used to facilitate the reaction.

General semicarbazone formation. Furthermore, where the heteroatom linker is a nitrogen atom, and the functional group present on one spacer linker or the releasable linker is an iminyl derivative, and the functional group present on the other spacer linker or the other releasable linker is an alkylamino or arylaminocarbonyl derivative, the required semicarbazone group can be formed by reacting the corresponding aldehyde or ketone, and a semicarbazide derivative, as illustrated in Scheme 10.

Scheme 10

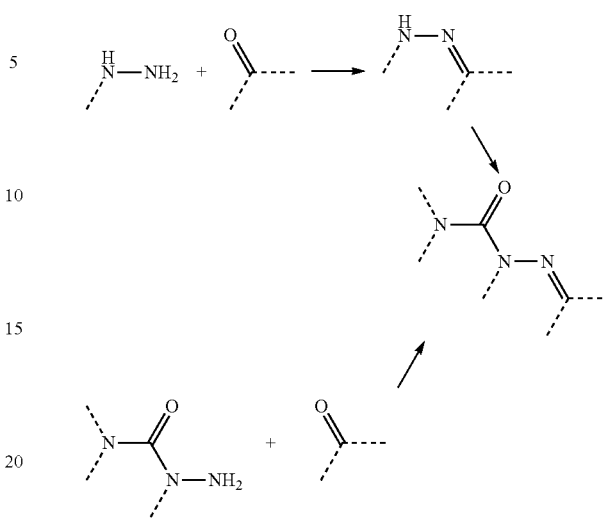

Solvents that can be used are THF, EtOAc, CH$_2$Cl$_2$, CHCl$_3$, CCl$_4$, DMF, DMSO, MeOH and the like. The temperature range employed in this transformation may vary between 0° C. and 80° C. Any acidic catalyst such as a mineral acid, H$_3$CCOOH, F$_3$CCOOH, p-TsOH.H$_2$O, pyridinium p-toluene sulfonate, and the like can be used. In addition, in forming the semicarbazone, the hydrazone functionality may be initially formed by reacting hydrazine with the corresponding aldehyde or ketone. The resulting hydrazone may subsequently by acylated with an isocyanate or a carbamoyl derivative, such as a carbamoyl halide, to form the semicarbazone. Alternatively, the corresponding semicarbazide may be formed by reacting hydrazine with an isocyanate or carbamoyl derivative, such as a carbamoyl halide to form a semicarbazide. Subsequently, the semicarbazide may be reacted with the corresponding aldehyde or ketone to form the semicarbazone.

General sulfonate formation. Furthermore, where the heteroatom linker is an oxygen atom, and the functional group present on the spacer linker or the releasable linker is sulfonyl derivative, the required sulfonate group can be formed by reacting the corresponding hydroxy-substituted compound with an activated sulfonyl derivative where L is a suitable leaving group such as halo, and the like, as illustrated in Scheme 11.

Scheme 11

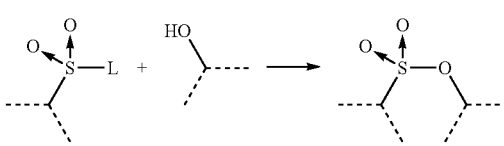

Solvents that can be used are THF, EtOAc, CH$_2$Cl$_2$, CHCl$_3$, CCl$_4$, and the like. The temperature range employed in this transformation may vary between 0° C. and 80° C. Any basic catalyst such as an inorganic base, an amine base, a polymer bound base, and the like can be used to facilitate the reaction.

General formation of folate-peptides. The folate-containing peptidyl fragment Pte-Glu-(AA)$_n$-NH(CHR$_2$)CO$_2$H (3) is prepared by a polymer-supported sequential approach using standard methods, such as the Fmoc-strategy on an acid-sensitive Fmoc-AA-Wang resin (1), as shown in Scheme 12.

Scheme 12

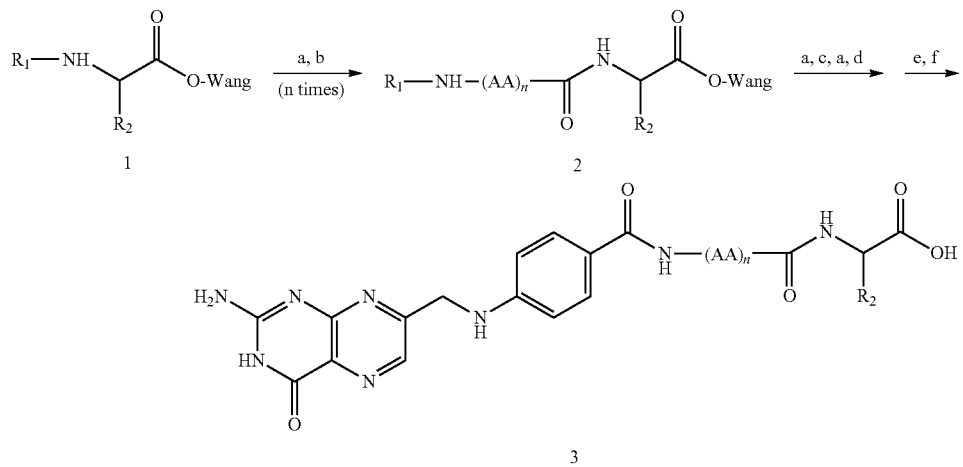

(a) 20% piperidine/DMF; (b) Fmoc—AA—OH, PyBop, DIPEA, DMF; (c) Fmoc-Glu(O—t-Bu)—OH, PyBop, DIPEA, DMF; (d) 1. $N^{10}$(TFA)-Pte-OH; PyBop, DIPEA, DMSO; (e) TFAA, $(CH_2)SH)_2$, i-$Pr_3$SiH; (f) $NH_4OH$, pH 10.3.

In this illustrative embodiment of the processes described herein, $R_1$ is Fmoc, $R_2$ is the desired appropriately-protected amino acid side chain, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, $N^{10}$-TFA-Pte-OH, and the like, are used, as described in Scheme 12, and represented in step (b) by Fmoc-AA-OH. Thus, AA refers to any amino acid starting material that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide 2, where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (O) to provide the folate-containing peptidyl fragment 3.

In another method of treatment embodiment, the group D in the targeted conjugate V-L-D, comprises an antigen (i.e., a compound that is administered for the purpose of eliciting an immune response in vivo), the ligand-antigen conjugates being effective to "label" the population of proximal tubule cells responsible for disease pathogenesis in the patient suffering from the kidney disease for specific elimination by an endogenous immune response or by co-administered antibodies. The use of ligand-antigen conjugates in the method of treatment described herein works to enhance an immune response-mediated elimination of the proximal tubule cells proliferating abnormally that overexpress the ligand receptor. Such elimination can be effected through an endogenous immune response or by a passive immune response effected by co-administered antibodies.

The methods of treatment involving the use of ligand-antigen conjugates are described in U.S. patent application Ser. Nos. 09/822,379, 10/138,275, and PCT Application Serial No. PCT/US04/014097, each incorporated herein by reference. The endogenous immune response can include a humoral response, a cell-mediated immune response, and any other immune response endogenous to the host animal, including complement-mediated cell lysis, antibody-dependent cell-mediated cytotoxicity (ADCC), antibody opsonization leading to phagocytosis, clustering of receptors upon antibody binding resulting in signaling of apoptosis, antiproliferation, or differentiation, and direct immune cell recognition of the delivered antigen (e.g., a hapten). It is also contemplated that the endogenous immune response may employ the secretion of cytokines that regulate such processes as the multiplication, differentiation, and migration of immune cells. The endogenous immune response may include the participation of such immune cell types as B cells, T cells, including helper and cytotoxic T cells, macrophages, natural killer cells, neutrophils, LAK cells, and the like.

The humoral response can be a response induced by such processes as normally scheduled vaccination, or active immunization with a natural antigen or an unnatural antigen or hapten, e.g., fluorescein isothiocyanate (FITC) or dinitrophenyl (DNP), with the unnatural antigen inducing a novel immunity. Active immunization involves multiple injections of the unnatural antigen or hapten scheduled outside of a normal vaccination regimen to induce the novel immunity. The humoral response may also result from an innate immunity where the host animal has a natural preexisting immunity, such as an immunity to α-galactosyl groups.

Alternatively, a passive immunity may be established by administering antibodies to the host animal such as natural antibodies collected from serum or monoclonal antibodies that may or may not be genetically engineered antibodies, including humanized antibodies. The utilization of a particular amount of an antibody reagent to develop a passive immunity, and the use of a ligand-antigen conjugate wherein the passively administered antibodies are directed to the antigen, would provide the advantage of a standard set of reagents to be used in cases where a patient's preexisting antibody titer to potential antigens is not therapeutically useful. The passively administered antibodies may be "co-administered" with the ligand-antigen conjugate, and co-administration is defined as administration of antibodies at a time prior to, at the same time as, or at a time following administration of the ligand-antigen conjugate.

The preexisting antibodies, induced antibodies, or passively administered antibodies will be redirected to the proximal tubule cells proliferating abnormally by binding of the ligand-antigen conjugates to the proximal tubule cell populations overexpressing the receptor for the ligand, and such pathogenic cells are killed or eliminated or reduced in number by complement-mediated lysis, ADCC, antibody-dependent phagocytosis, or antibody clustering of receptors. The cytotoxic process may also involve other types of immune responses, such as cell-mediated immunity.

Acceptable antigens for use in preparing the conjugates used in the method of treatment described herein are antigens that are capable of eliciting antibody production in a patient or animal or that have previously elicited antibody production in a patient or animal, resulting in a preexisting immunity, or that constitute part of the innate immune system. Alternatively, antibodies directed against the antigen may be administered to the patient or animal to establish a passive immunity. Suitable antigens for use in the invention include antigens or antigenic peptides against which a preexisting immunity has developed via normally scheduled vaccinations or prior natural exposure to such agents such as polio virus, tetanus, typhus, rubella, measles, mumps, pertussis, tuberculosis and influenza antigens, and α-galactosyl groups. In such cases, the ligand-antigen conjugates will be used to redirect a previously acquired humoral or cellular immunity to a population of proximal tubule cells proliferating abnormally in the patient or animal for elimination of the proximal tubule cells or reduction in number or inactivation, completely or partially.

Other suitable immunogens include antigens or antigenic peptides to which the host animal has developed a novel immunity through immunization against an unnatural antigen or hapten, for example, fluorescein isothiocyanate (FITC) or dinitrophenyl, and antigens against which an innate immunity exists, for example, super antigens and muramyl dipeptide.

The proximal tubule cell-binding ligands and antigens, cytotoxic agents, and cell growth inhibitors, or diagnostic markers, as the case may be, in forming conjugates for use in accordance with the methods described herein can be conjugated by using any art-recognized method for forming a complex. This can include covalent, ionic, or hydrogen bonding of the ligand V to the group D compound, either directly or indirectly via a linking group such as a divalent linker. The conjugate is typically formed by covalent bonding of the ligand to the targeted entity through the formation of amide, ester or imino bonds between acid, aldehyde, hydroxy, amino, or hydrazo groups on the respective components of the complex or, for example, by the formation of disulfide bonds. Methods of linking binding ligands to antigens, cytotoxic agents, or cell growth inhibitors, or diagnostic markers are described in U.S. patent application Ser. Nos. 10/765,336 and 60/590,580, each incorporated herein by reference.

Alternatively, as mentioned above, the ligand complex can be one comprising a liposome wherein the targeted entity (that is, the diagnostic marker, or the antigen, cytotoxic agent or cell growth inhibitor) is contained within a liposome which is itself covalently linked to the binding ligand. Other nanoparticles, dendrimers, derivatizable polymers or copolymers that can be linked to therapeutic or diagnostic markers useful in the treatment and diagnosis of kidney disease states can also be used in targeted conjugates.

In one embodiment of the invention the ligand is folic acid, an analog of folic acid, or any other folate receptor binding molecule, and the folate ligand is conjugated to the targeted entity by a procedure that utilizes trifluoroacetic anhydride to prepare γ-esters of folic acid via a pteroyl azide intermediate. This procedure results in the synthesis of a folate ligand, conjugated to the targeted entity only through the γ-carboxy group of the glutamic acid groups of folate. Alternatively, folic acid analogs can be coupled through the α-carboxy moiety of the glutamic acid group or both the α and γ carboxylic acid entities.

The therapeutic methods described herein can be used to slow the progress of disease completely or partially. Alternatively, the therapeutic methods described herein can eliminate or prevent reoccurrence of the disease state.

The conjugates used in accordance with the methods described herein of the formula V-L-D are used in one aspect to formulate therapeutic or diagnostic compositions, for administration to a patient or animal, wherein the compositions comprise effective amounts of the conjugate and an acceptable carrier therefore. Typically such compositions are formulated for parenteral use. The amount of the conjugate effective for use in accordance with the methods described herein depends on many parameters, including the nature of the disease being treated or diagnosed, the molecular weight of the conjugate, its route of administration and its tissue distribution, and the possibility of co-usage of other therapeutic or diagnostic agents. The effective amount to be administered to a patient or animal is typically based on body surface area, patient weight and physician assessment of patient condition. An effective amount can range from about to 1 ng/kg to about 1 mg/kg, more typically from about 1 μg/kg to about 500 μg/kg, and most typically from about 1 μg/kg to about 100 μg/kg.

Any effective regimen for administering the ligand conjugates can be used. For example, the ligand conjugates can be administered as single doses, or they can be divided and administered as a multiple-dose daily regimen. Further, a staggered regimen, for example, one to three days per week can be used as an alternative to daily treatment, and such an intermittent or staggered daily regimen is considered to be equivalent to every day treatment and within the scope of this disclosure. In one embodiment, the patient or animal is treated with multiple injections of the ligand conjugate wherein the targeted entity is an antigen or a cytotoxic agent or a cell growth inhibitor to eliminate the population of pathogenic proximal tubule cells. In one embodiment, the patient or animal is treated, for example, injected multiple times with the ligand conjugate at, for example, 12-72 hour intervals or at 48-72 hour intervals. Additional injections of the ligand conjugate can be administered to the patient or animal at intervals of days or months after the initial injections, and the additional injections prevent recurrence of disease. Alternatively, the ligand conjugates may be administered prophylactically to prevent the occurrence of disease in patients or animals known to be disposed to development of kidney disease states. In one embodiment, more than one type of ligand conjugate can be used, for example, the patient or animal may be pre-immunized with fluorescein isothiocyanate and dinitrophenyl and subsequently treated with fluorescein isothiocyanate and dinitrophenyl linked to the same or different targeting ligands in a co-dosing protocol.

The ligand conjugates are administered in one aspect parenterally and most typically by intraperitoneal injections, subcutaneous injections, intramuscular injections, intravenous injections, intradermal injections, or intrathecal injections. The ligand conjugates can also be delivered to a patient or animal using an osmotic pump. Examples of parenteral dosage forms include aqueous solutions of the conjugate, for example, a solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate. In another aspect, the ligand conjugates can be formulated as one of any of a number of prolonged release dosage forms known in the art such as, for example, the biodegradable carbohydrate matrices described in U.S. Pat. Nos. 4,713,249; 5,266,333; and 5,417,982, the disclosures of which are incorporated herein by reference. The ligand conjugates can also be administered topically such as in an ointment or a lotion, for example, or in a patch form.

The following examples are illustrative embodiments only and are not intended to be limiting.

Example 1

Materials

Fmoc-protected amino acid derivatives, trityl-protected cysteine 2-chlorotrityl resin (H-Cys(Trt)-2-ClTrt resin #04-12-2811), Fmoc-lysine(4-methyltrityl) wang resin, 2-(1H-benzotriaxol-1-yl)-1,1,3,3-tetramethyluronium hexafluorophosphage (HBTU) and N-hydroxybenzotriazole can be purchased from Novabiochem (La Jolla, Calif.). $N^{10}$-trifluoroacetylpteroic acid can be purchased from Sigma, St. Louis, Mo.

Example 2

Systhesis of Folate-Cysteine

Standard Fmoc peptide chemistry can be used to synthesize folate-cysteine with the cysteine attached to the γ-COOH of folic acid. The sequence Cys-Glu-Pteroic acid (Folate-Cys) will be constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid will be linked to a trityl-protected Cys linked to a 2-Chlorotrityl resin. $N^{10}$-trifluoroacetylpteroic acid was then attached to the γ-COOH of Glu. The Folate-Cys was cleaved from the resin using a 92.5% trifluoroacetic acid-2.5% water-2.5% triisopropylsilane-2.5% ethanedithio solution. Diethyl ether will be used to precipitate the product, and the precipitant was collected by centrifugation. The product will be washed twice with diethyl ether and dried under vacuum overnight. To remove the $N^{10}$-trifluoracetyl protecting group, the product will be dissolved in a 10% ammonium hydroxide solution and stirred for 30 min at room temperature. The solution will be kept under a stream of nitrogen the entire time in order to prevent the cysteine from forming disulfides. After 30 minutes, hydrochloric acid will be added to the solution until the compound precipitates. The product will be collected by centrifugation and lyophilized. The product will be analyzed and confirmed by mass spectroscopic analysis.

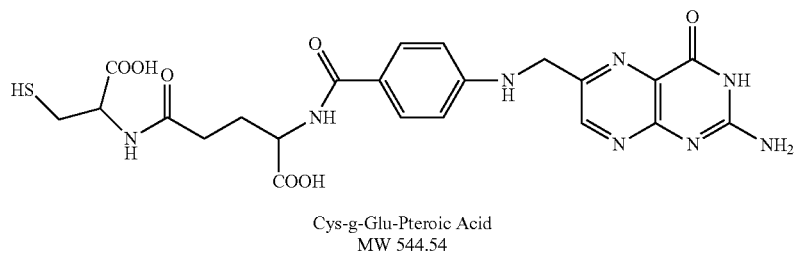 [SMILES: Nc1nc2ncc(CNc3ccc(C(=O)NC(CCC(=O)NC(CS)C(=O)O)C(=O)O)cc3)nc2c(=O)[nH]1]

Cys-g-Glu-Pteroic Acid
MW 544.54

Example 3

Synthesis of Folate R-Phycoerythrin

Folate-phycoerythrin will be synthesized by following a procedure published by Kennedy M.D. et al. in *Pharmaceutical Research*, Vol. 20(5); 2003. Briefly, a 10-fold excess of folate-cysteine will be added to a solution of R-phycoerythrin pyridyldisulfide (Sigma, St. Louis, Mo.) in phosphate buffered saline (PBS), pH 7.4. The solution will be allowed to react overnight at 4° C. and the labeled protein (Mr ~260 kDa) will be purified by gel filtration chromatography using a G-15 desalting column. The folate labeling will be confirmed by fluorescence microscopy of M109 cells incubated with folate-phycoerythrin in the presence and absence of 100-fold excess of folic acid. After a 1-h incubation and 3 cells washes with PBS, the treated cells will be intensely fluorescent, while the sample in the presence of excess folic acid will show little cellular fluorescence.

Example 4

Synthesis of Folate-Fluorescein

Folate-FITC will be synthesized as described by Kennedy, M. D. et al. in *Pharmaceutical Research*, Vol. 20(5); 2003.

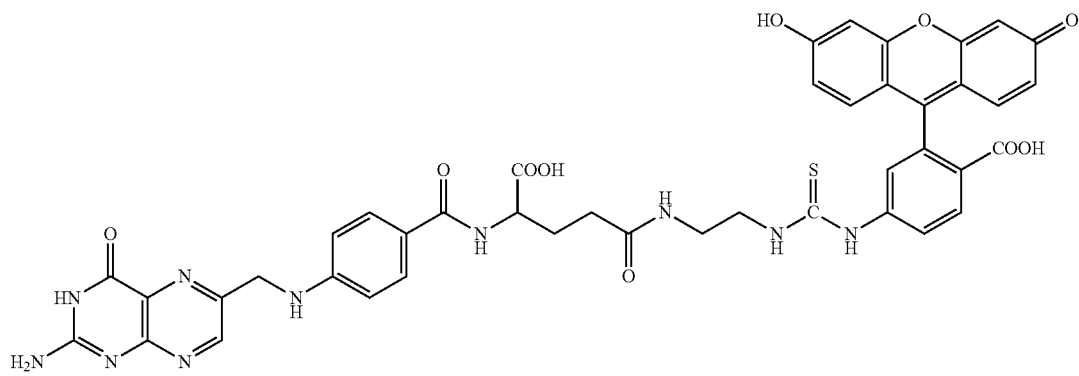

Folate-EDA-FITC
MW 888.90

Example 5

Liposome Preparation

Liposomes will be prepared following methods by Leamon et al. in *Bioconjugate Chemistry* 2003, 14, 738-747. Briefly, lipids and cholesterol will be purchased from Avanti Polar Lipids (Alabaster, Ala.). Folate-targeted liposomes will consist of 40 mole % cholesterol, either 4 mole % or 6 mole % polyethyleneglycol (Mr~2000)-derivatized phosphatidylethanolamine (PEG2000-PE, Nektar, Ala., Huntsville, Ala.), either 0.03 mole % or 0.1 mole % folate-cysteine-PEG3400-PE and the remaining mole % will be composed of egg phosphatidylcholine. Non-targeted liposomes will be prepared identically with the absence of folate-cysteine-PEG3400-PE. Lipids in chloroform will be dried to a thin film by rotary evaporation and then rehydrated in PBS containing the drug. Rehydration will be accomplished by vigorous vortexing followed by 10 cycles of freezing and thawing. Liposomes will be extruded 10 times through a 50 nm pore size polycarbonate membrane using a high-pressure extruder (Lipex Biomembranes, Vancouver, Canada).

Example 6

Synthesis of Folate-Saporin

The protein saporin will be purchased from Sigma (St. Louis, Mo.). Folate-saporin will be prepared following folate-protein conjugation methods published by Leamon and Low in The Journal of Biological Chemistry 1992, 267 (35); 24966-24971. Briefly, folic acid will be dissolved in DMSO and incubated with a 5 fold molar excess of 1-ethyl-3-(3-dimethylaminopropyl)carbodiimide for 30 minutes at room temperature. The saporin will be dissolved in 100 mM $KH_2PO_4$, 100 mM boric acid, pH 8.5. A 10-fold molar excess of the "activated" vitamin will be added to the protein solution and the labeling reaction will be allowed to proceed for 4 hours. Unreacted material will be separated from the labeled protein using a Sephadex G-25 column equilibrated in phosphate-buffered saline, pH 7.4.

Example 7

Synthesis of Folate-Peptides

Generally, the reagents shown in the following table were used in the preparation of this example and other examples:

| Reagent | (mmol) | equivalents | Amount |
|---|---|---|---|
| H-Cys(4-methoxytrityl)-2-chlorotrityl-Resin (loading 0.56 mmol/g) | 0.56 | 1 | 1.0 g |
| Fmoc-β-aminoalanine(NH-MTT)-OH | 1.12 | 2 | 0.653 g |
| Fmoc-Asp(OtBu)-OH | 1.12 | 2 | 0.461 g |
| Fmoc-Asp(OtBu)-OH | 1.12 | 2 | 0.461 g |
| Fmoc-Asp(OtBu)-OH | 1.12 | 2 | 0.461 g |
| Fmoc-Glu-OtBu | 1.12 | 2 | 0.477 g |
| $N^{10}$TFA-Pteroic Acid (dissolve in 10 ml DMSO) | 0.70 | 1.25 | 0.286 g |
| DIPEA | 2.24 | 4 | 0.390 mL |
| PyBOP | 1.12 | 2 | 0.583 g |

The coupling step was performed as follows: In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 6 coupling steps. At the end wash the resin with 2% hydrazine in DMF 3× (5 min) to cleave TFA protecting group on Pteroic acid.

Cleave the peptide analog from the resin using the following reagent, 92.5% (50 ml) TFA, 2.5% (1.34 ml) $H_2O$, 2.5% (1.34 ml) Triisopropylsilane, 2.5% (1.34 ml) ethanedithiol, the cleavage step was performed as follows: Add 25 ml cleavage reagent and bubble for 1.5 hr, drain, and wash 3× with remaining reagent. Evaporate to about 5 mL and precipitate in ethyl ether. Centrifuge and dry. Purification was performed as follows: Column-Waters NovaPak $C_{18}$ 300×19mm; Buffer A=10 mM Ammonium Acetate, pH 5; B=CAN; 1% B to 20% B in 40 minutes at 15 ml/min, to 350 mg (64%); HPLC-RT 10.307 min., 100% pure, $^1$H HMR spectrum consistent with the assigned structure, and MS (ES-): 1624.8, 1463.2, 1462.3, 977.1, 976.2, 975.1, 974.1, 486.8, 477.8.

Example 8

Synthesis of Folate-γ-Asp-Arg-Asp-Asp-Cys

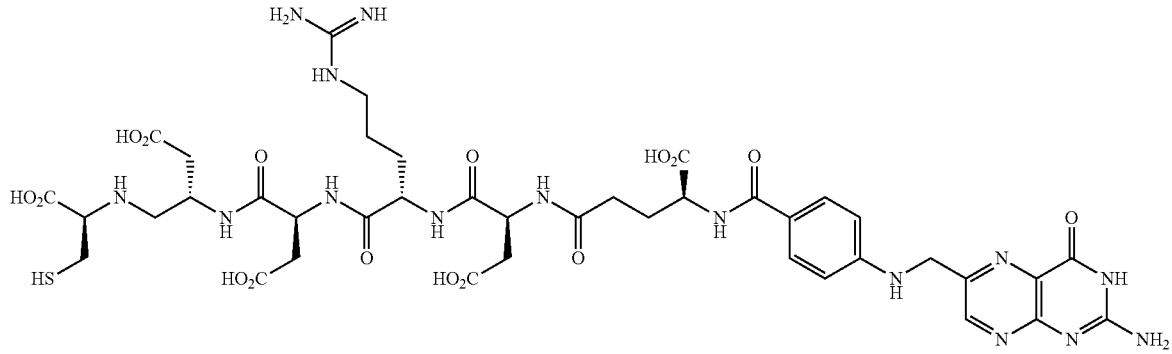 [SMILES: N=C(N)NCCC[C@H](NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CC(=O)O)C(=O)N[C@H](CN[C@@H](CS)C(=O)O)CC(=O)O]

According to the general procedure of the prior example and Scheme 12, Wang resin bound 4-methoxytrityl (MTT)-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. Selected $^1$H NMR (D$_2$O) δ (ppm) 8.68 (s, 1H, FA H-7), 7.57 (d, 2H, J=8.4 Hz, FA H-12 & 16), 6.67 (d, 2H, J=9 Hz, FA H-13 & 15), 4.40-4.75 (m, 5H), 4.35 (m, 2H), 4.16 (m, 1H), 3.02 (m, 2H), 2.55-2.95 (m, 8H), 2.42 (m, 2H), 2.00-2.30 (m, 2H), 1.55-1.90 (m, 2H), 1.48 (m, 2H); MS (ESI, m+H$^+$) 1046.

Example 9

Synthesis of Folate-γ-Asp-Asp-Asp-(β-NH$_2$-Ala)-Cys

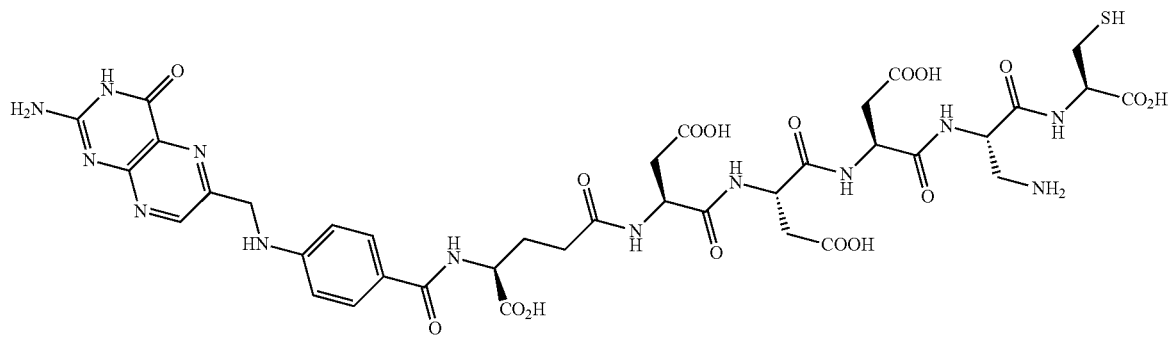 [SMILES: NC[C@H](NC(=O)[C@H](CC(=O)O)NC(=O)[C@H](CC(=O)O)NC(=O)[C@H](CC(=O)O)NC(=O)CC[C@H](NC(=O)c1ccc(NCc2cnc3nc(N)[nH]c(=O)c3n2)cc1)C(=O)O)C(=O)N[C@@H](CS)C(=O)O]

According to the general procedure of the prior example and Scheme 12, Wang resin bound 4-methoxytrityl (MTT)-protected Cys-NH$_2$ was reacted according to the following sequence: 1) a. Fmoc-β-aminoalanine(NH-MTT)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Asp(OtBu)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu-OtBu, PyBOP, DIPEA; b. 20% Piperidine/DMF; 6) N$^{10}$-TFA-pteroic acid, PyBOP, DIPEA. The MTT, tBu, and TFA protecting groups were removed with a. 2% hydrazine/DMF; b. TFA/H$_2$O/TIPS/EDT (92.5:2.5:2.5:2.5).

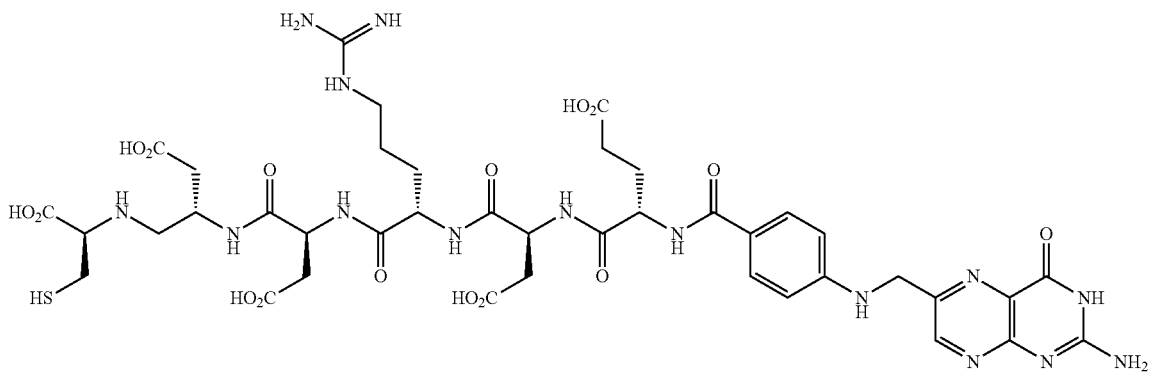 [SMILES: N=C(N)NCCC[C@H](NC(=O)[C@H](CC(=O)O)NC(=O)[C@H](CCC(=O)O)NC(=O)c1ccc(NCc2cnc3nc(N)[nH]c(=O)c3n2)cc1)C(=O)N[C@@H](CC(=O)O)C(=O)N[C@H](CN[C@@H](CS)C(=O)O)CC(=O)O]

Example 10

Synthesis of Folate-α-Asp-Arg-Asp-Asp-Cys

According to the general procedure of the prior example and Scheme 12, Wang resin bound MTT-protected Cys-NH$_2$ was reacted according to the following sequence: 1) a. Fmoc-Asp(OtBu)-OH, PyBOP, DIPEA; b. 20% Piperidine/DMF; 2) a. Fmoc-Asp(OtBu)-OH, PyBOP, DIPEA; b. 20% Piperidine/DMF; 3) a. Fmoc-Arg(Pbf)-OH, PyBOP, DIPEA; b. 20% Piperidine/DMF; 4) a. Fmoc-Asp(OtBu)-OH, PyBOP, DIPEA; b. 20% Piperidine/DMF; 5) a. Fmoc-Glu(γ-OtBu)-OH, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

Example 11

Synthesis of Folate-γ-D-Asp-D-Arg-D-Asp-D-Asp-D-Cys

According to the general procedure of the prior example and Scheme 12, Wang resin bound MTT-protected D-Cys-NH$_2$ was reacted according to the following sequence: 1) a. Fmoc-D-Asp(OtBu)-OH, PyBOP, DIPEA; b. 20% Piperidine/DMF; 2) a. Fmoc-D-Asp(OtBu)-OH, PyBOP, DIPEA; b. 20% Piperidine/DMF; 3) a. Fmoc-D-Arg(Pbf)-OH, PyBOP, DIPEA; b. 20% Piperidine/DMF; 4) a. Fmoc-D-Asp(OtBu)-OH, PyBOP, DIPEA; b. 20% Piperidine/DMF; 5) a. Fmoc-D-Glu-OtBu, PyBOP, DIPEA; b. 20% Piperidine/DMF; 6) N$^{10}$-TFA-pteroic acid, PyBOP, DIPEA. The MTT, tBu, and Pbf protecting groups were removed with TFA/H$_2$O/TIPS/EDT (92.5:2.5:2.5:2.5), and the TFA protecting group was removed with aqueous NH$_4$OH at pH=9.3. The $^1$H NMR spectrum was consistent with the assigned structure.

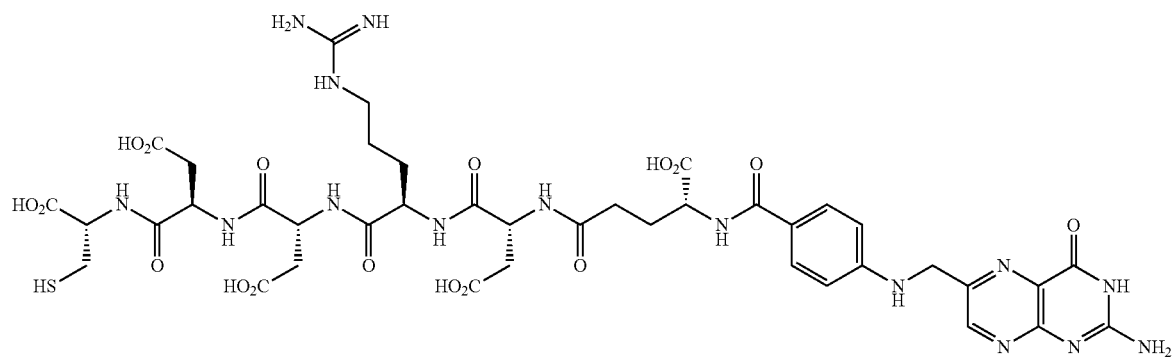 [SMILES: N=C(N)NCCC[C@@H](NC(=O)[C@@H](CC(=O)O)NC(=O)CC[C@@H](NC(=O)c1ccc(NCc2cnc3nc(N)[nH]c(=O)c3n2)cc1)C(=O)O)C(=O)N[C@H](CC(=O)O)C(=O)N[C@H](CC(=O)O)C(=O)N[C@H](CS)C(=O)O]

45

Example 12

Synthesis of Folate-Rapamycin (EC0371)

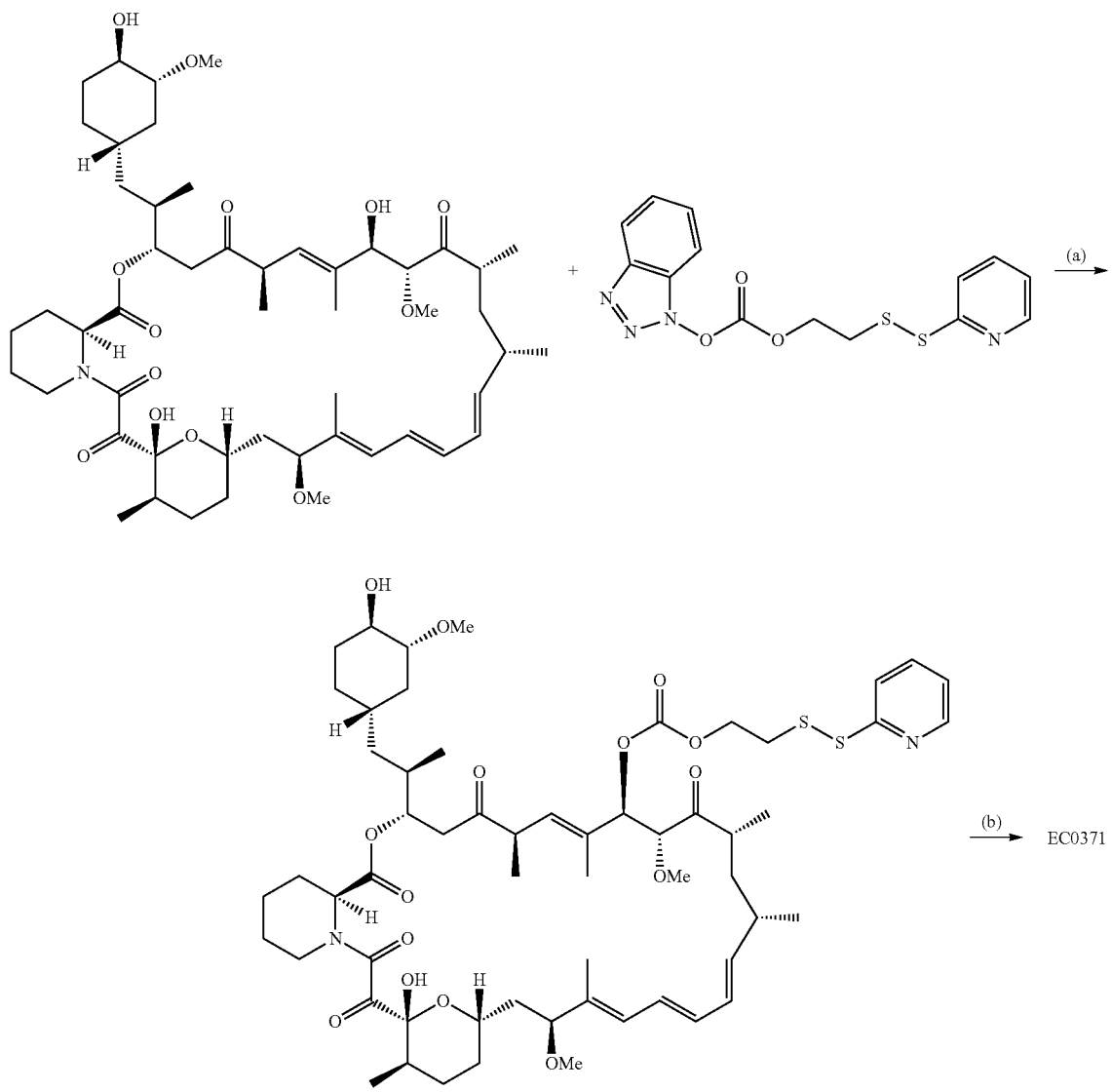

(a) DMAP, CH2Cl2, 70%; (b) folate-γ-Asp-Arg-Asp-Asp-Cys, DIPEA, DMSO 60%.

This example was prepared according to the prior scheme and the processes described herein.

Example 13

Animal Models

To test the ligand-cytotoxin, ligand-antigen, and ligand-cell growth inhibitor conjugates in animal models of PKD, well-established animal models will be used. Those animal models are described in Shillingford, et al., PNAS 103: 5466-5471 (2006), Piontek, et al., J. Am. Soc. Nephrol. vol. 15: 3035-3043 (2004), Brown, et al., Kidney Int. vol. 63: 1220-1229 (2003), and Nauta, et al., Pediatr. Nephrol. vol. 7: 163-172 (1993), incorporated herein by reference.

46

Example 14

Immunofluorescence

Figure 6:
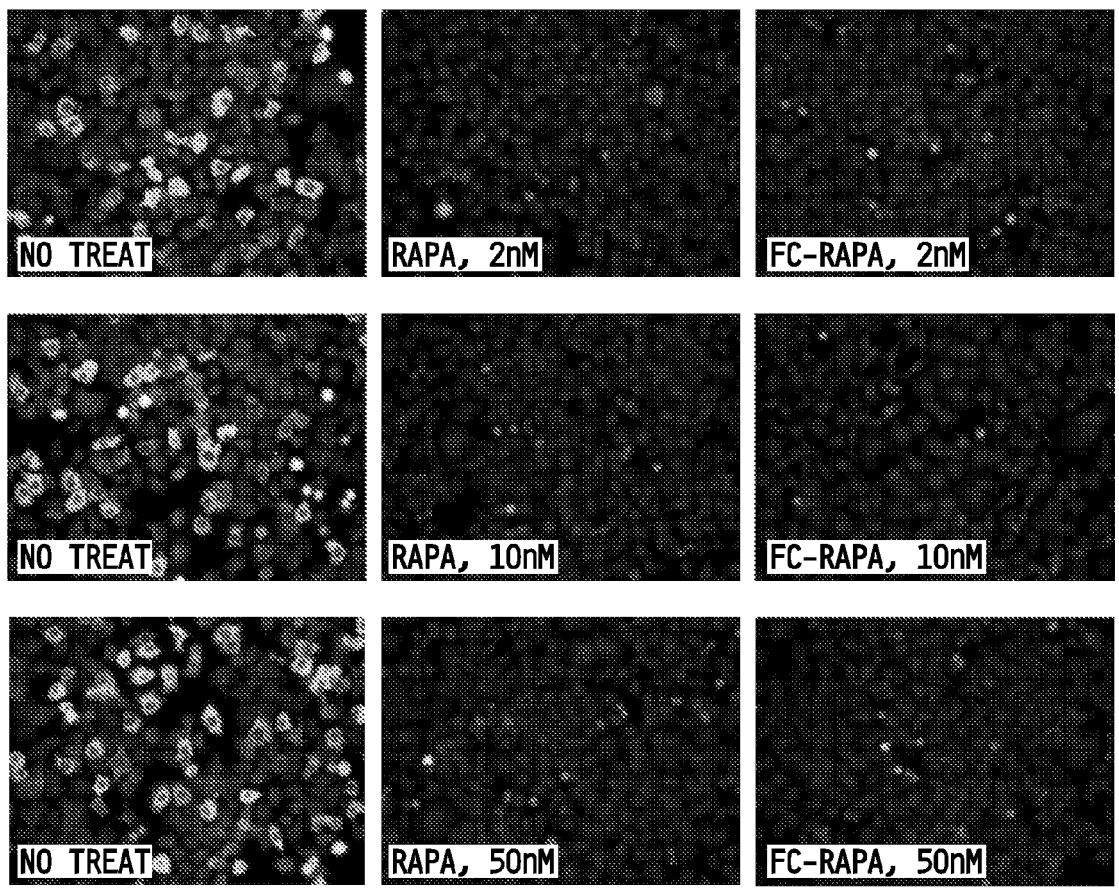
FIG. 6 shows the effects of rapamycin and EC0371 on P-S6 immunostaining in KB cells after 16 hours of incubation with rapamycin or EC0371. P-S6 is a phosphorylation target of m-TOR and the antibody used is phospho-specific. The leftmost panels show untreated cells. The panels in the middle column show cells treated with 2, 10, or 50 nM rapamycin. The panels in the rightmost column show cells treated with 2, 10, or 50 nM EC0371. Rapamycin and EC0371 inhibit P-S6 immunostaining (i.e., phosphorylation of P-S6 through the mTOR pathway).

The ability of folate-conjugated rapamycin to inhibit the mTOR pathway was tested in KB cells using immunostaining for P-S6 as a marker (see FIG. 6). The immunostaining procedure was performed according to the following protocol:

1. Aspirate media from cells and immediately add 1 ml/well of 10% neutral-buffered formalin (NBF) to each well.

2. Fix cells for 15 minutes at room temp with gentle orbital shaking.

3. Aspirate NBF from cells and wash briefly with 2 changes (1 ml/well) of 1×PBS.

4. Aspirate PBS and add 1 ml of quench solution and quench for 10 minutes at room temperature with gentle orbital shaking.

5. Aspirate quench and wash briefly with 2 changes (1 ml/well) of 1×PBS.

6. Aspirate PBS and add 1 ml/well cell block/permeabilization (CBP) solution and incubate for 30 minutes at 37° C.

7. Prepare P-S6 (S235/6)/β-tubulin antibody solution by diluting antibody 1:200 in CBP solution (for 12 coverslips make 1194 ul CBP+6 ul P-S6 and β-tubulin). Mix thoroughly.

8. Remove the lid from the cell culture dish and place in a humidified chamber. Cut parafilm to the size of the lid and press firmly on to the lid.

9. Using a pair of needle-nose tweezers transfer a coverslip, cell-side up, to its corresponding well position on the lid. Pipet 150 µl of P-S6/β-tubulin antibody solution onto the coverslip. Repeat for all remaining coverslips.

10. Close the lid and incubate overnight at 4° C.

11. The following day, make 100 ml cell wash (CW) solution.

12. Pipet 1 ml CW solution into each well of a fresh 12-well plate. Using two pairs of tweezers, one placed on the back of the coverslip, carefully pick up the coverslip and place back in the corresponding well.

13. Incubate for 5 minutes with gentle orbital shaking. Aspirate and repeat wash 2×.

14. During washes, dilute fluorescent-conjugated anti-rabbit FITC and anti-mouse TXR secondary antibodies 1:200 in CBP. Centrifuge 10 minutes at 4° C., 13,000 rpm, to remove aggregates.

15. After washing, repeat steps 8 and 9 with diluted fluorescent-conjugated secondary antibody solution. Incubate for 1 hour at 37° C.

16. Repeat steps 12 and 13.

17. Rinse 1× with 1×PBS.

18. Aspirate and wash 2×3 minutes with 1×PBS+0.1% Triton-X 100 with gentle orbital shaking.

19. Aspirate and rinse 2× with 1×PBS.

20. Aspirate and add 1 ml of 10% NBF to post-fix secondary antibodies. Incubate for 10 minutes at room temperature with gentle orbital shaking.

21. Aspirate and wash 1×5 minutes with 1×PBS.

22. Aspirate and add 1 ml of 1×PBS+DAPI (1 mg/ml stock, 1:50,000 dilution). Incubate for 5-10 minutes.

23. Thaw Prolong Gold mounting medium. Dispense two drops on a slide. Using needle-nose tweezers remove individual coverslips, wipe excess solution from backside and place on top of mounting medium, cell-side down. Gently squeeze out any air bubbles with the opposite end of the tweezers.

25. Allow mounting medium to harden for at least 1 hour, preferably overnight. View slides under a suitable microscope equipped for fluorescence. Store slides at −20° C.

Example 15

Folate Receptor Immunohistochemistry

Figure 2:
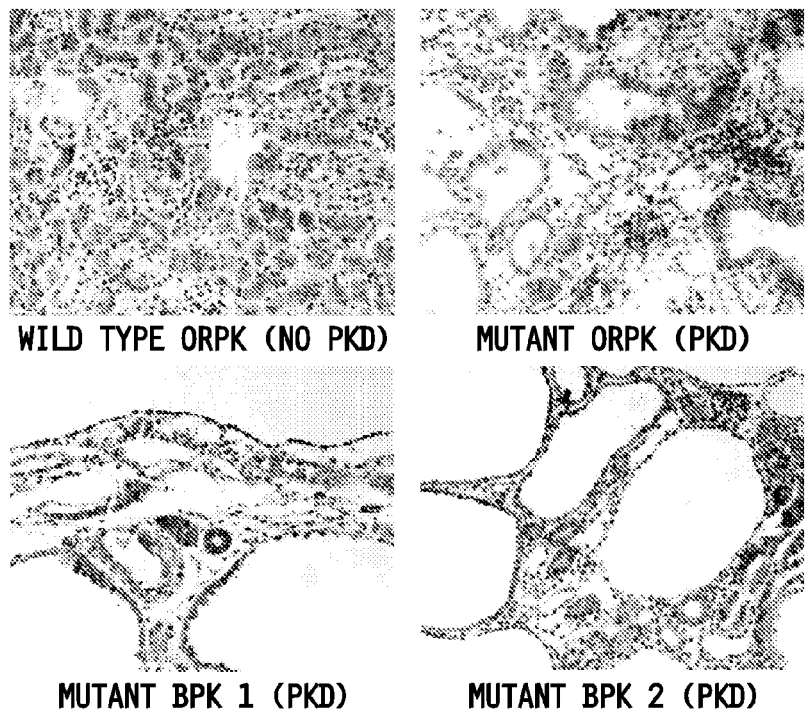
FIG. 2 shows IHC analysis of folate receptor expression in polycystic kidney disease tissues using a polyclonal antibody directed to the folate receptor for staining. The upper left panel shows normal mouse kidney tissue and the remainder of the panels show staining of cysts in polycystic kidney disease tissues using the anti-folate receptor polyclonal antibody.

Immunohistochemistry was performed as described in PCT Publ. No. WO/2006/105141, incorporated herein by reference. As shown in FIGS. 1 and 2, monoclonal and polyclonal antibodies to the folate receptor stain cysts in polycystic kidney disease tissues indicating folate receptor overexpression in the cells that form PKD cysts (see also Table 1 below).

TABLE 1

Polycystic Kidney Tissue from Mice and Humans
Polycystic Kidney Disease IHC Results

| | Specimen ID | 3+ | 2+ | 1+ | 0 |
|---|---|---|---|---|---|
| PKD | PKD Case 7 | 10% | 30% | 40% | 20% |
| | PKD Case 8 | 0% | 30% | 60% | 10% |
| | PKD Case 9 | 0% | 10% | 20% | 70% |
| | PKD Case 10 | 0% | 0% | 40% | 60% |
| Control Kidney | N1 | 10% | 20% | 30% | 40% |
| | N3 | Tissue was not normal kidney | | | |
| | N4 | 30% | 30% | 30% | 10% |
| Serous OVCA | ITOC02407A | 0% | 20% | 50% | 30% |
| | ITOC02463A | 10% | 20% | 10% | 60% |
| | ITOC02556A | 0% | 0% | 0% | 100% |
| PKD | ORPK666B | 10% | 10% | 50% | 30% |
| | BPK6468D | 0% | 10% | 20% | 70% |
| | BPK6467B | 0% | 20% | 40% | 40% |
| Control Kidney | ORPK665B | 0% | 0% | 40% | 60% |
| | ORPK667B | 0% | 5% | 80% | 15% |
| | BPK6466B | 0% | 5% | 75% | 20% |
| | BPK6469B | 0% | 0% | 0% | 100% |

Example 16

Relative Affinity Assay

Figure 4:
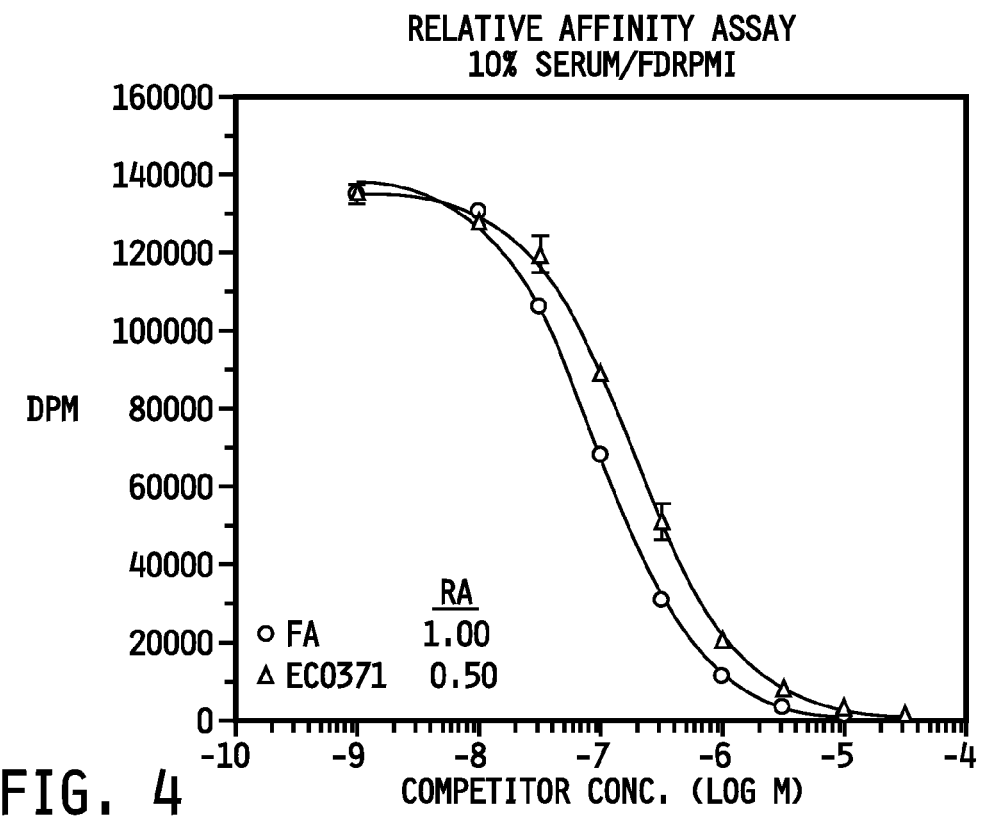
FIG. 4 shows an affinity assay comparing the relative affinities of folic acid (circles; 1.0) and EC0371 (triangles; 0.5) for the folate receptor.

Binding assays were run to determine the relative affinities of EC0371 and folic acid at the folate receptor. KB cells were incubated for 1 hour at 37° C. with 100 nM $^3$H-folic acid in the presence and absence of increasing competitor concentrations. As shown in FIG. 4 (error bars represent 1 standard deviation (n=3)), the relative affinity of EC0371 at the folate receptor is 0.5 compared to a relative affinity of 1.0 for folic acid.

Example 17

Cell Viability

Figure 5:
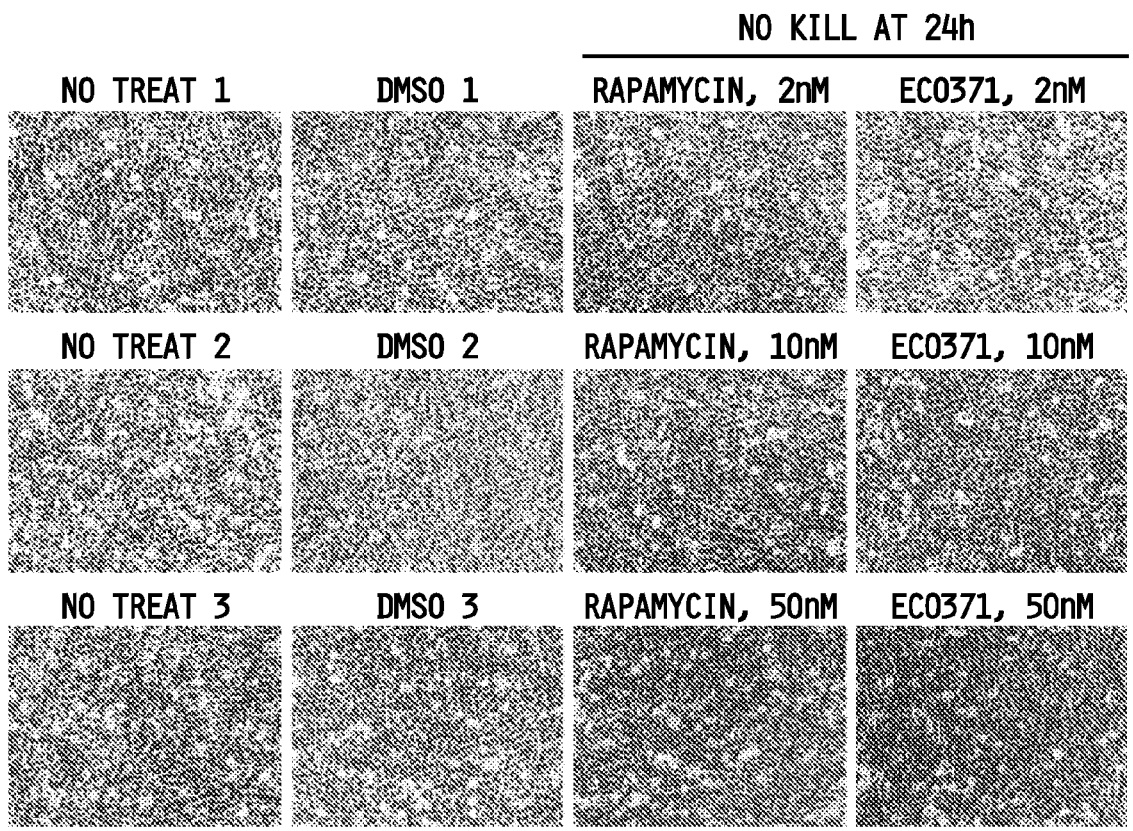
FIG. 5 shows the effect of rapamycin and EC0371 on the viability of KB cells at various free rapamycin and conjugated rapamycin (EC0371) concentrations. The leftmost panels show untreated cells. The panels in the second column from the left show control cells treated with DMSO (diluent). The panels in the third column from the left show cells treated with 2, 10, or 50 nM rapamycin. The panels in the rightmost column show cells treated with 2, 10, or 50 nM EC0371. Neither rapamycin nor EC0371 is cytotoxic after 24 hours of treatment.

Cell viability was examined in KB cells following incubation for 16 hours in Rapamycin (2, 10, and 50 nM), EC0371 (2, 10, and 50 nM), DMSO (diluent), and media alone (FIG. 5). At 24 hours, neither rapamycin nor EC0371 was found to be cytotoxic at any of the concentrations tested.

Example 18

P-S6 and P-S6K Immunoblots

Figure 7:
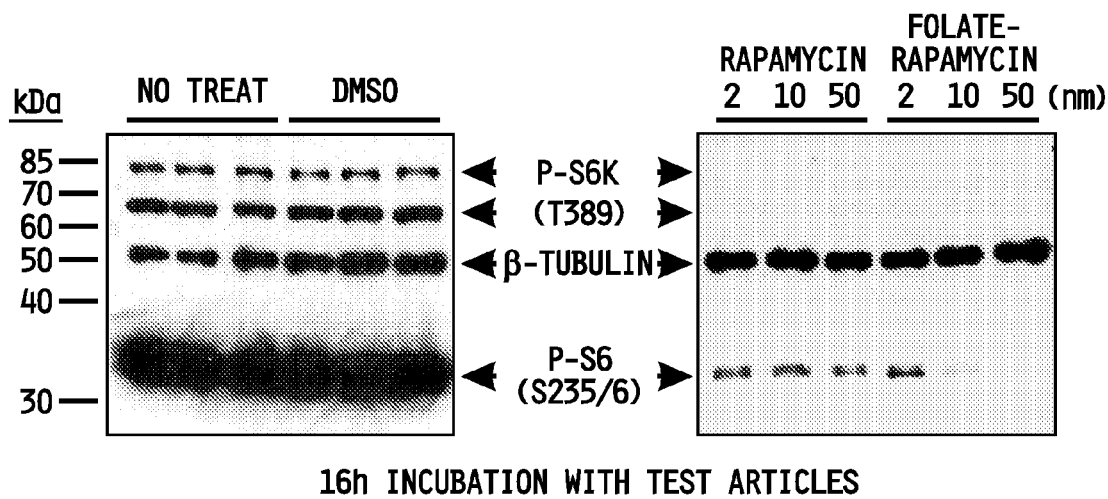
FIG. 7 shows an immunoblot using a phospho-specific antibody. The left panel shows phosphorylation of ribosomal S6 and S-6 kinase (T389) in untreated cells and cells treated with DMSO (diluent). The right panel shows that rapamycin (2, 10, and 50 nM) and EC0371 (folate-rapamyin; 2, 10, and 50 nM) abolish or greatly reduce phosphorylation of ribosomal S6 and S-6 kinase (T389) which are phosphorylation targets in the m-TOR pathway.

Folate-rapamycin was found to be highly effective in inhibiting mTOR in cultured cells. Folate receptor-positive KB cells were treated with either unconjugated rapamycin (2, 10, or 50 nM) or folate-rapamycin (2, 10, or 50 nM) for 16 hours. The activity of mTOR was determined by immunoblotting using phospho-specific antibodies against P-S6 and P-S6K (FIG. 7).

Example 19

Therapeutic Effects of EC0371 In Vivo

The therapeutic effect of EC0371 (folate-conjugated rapamycin) was tested on in vivo development of polycystic kidney disease in the bpk-mutant mouse model. Bpk-mutant mice develop polycystic kidney disease (PKD) starting at embryogenesis due to a point mutation in the gene encoding bicaudal C. All nephron segments are affected, and most bpk-mutant mice die between postnatal days 24-30 due to severely enlarged cystic kidneys and renal failure.

All mice were genotyped by PCR prior to treatment. Wild-type (Wt) and bpk-mutant (bpk) mice were then segregated into the following three groups: no treatment (n=5 Wt, 2 bpk); vehicle treatment (n=5 Wt, 3 bpk); and EC0371 treatment (n=4 Wt, 4 bpk).

Figure 8:
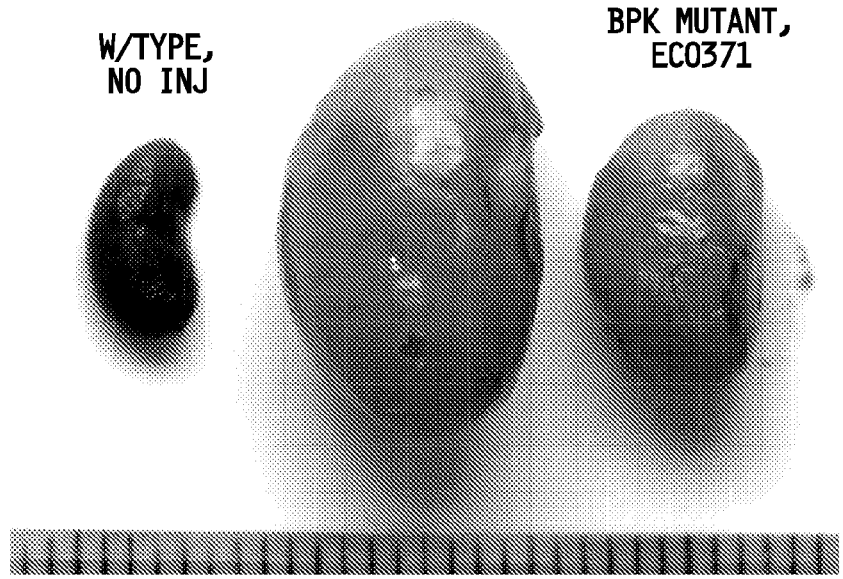
FIG. 8 shows the therapeutic effect of EC0371 on the in vivo development of polycystic kidney disease in the bpk-mutant mouse model. The leftmost kidney is from a wildtype mouse. The middle kidney is from a bpk mutant mouse not treated with EC0371. The rightmost kidney is from a bpk mutant mouse treated with EC0371 showing that EC0371 greatly reduces kidney size.
Figure 9:
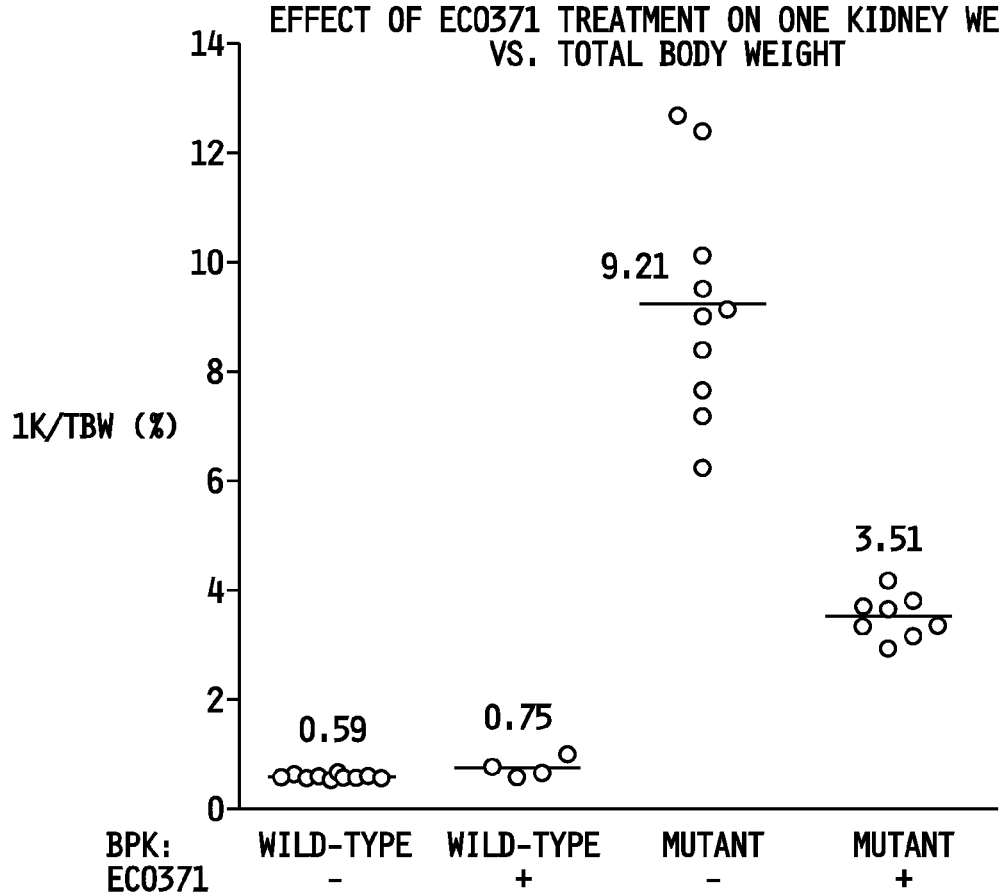
FIG. 9 shows the effect on one-kidney weight of EC0371 treatment in multiple bpk mutant mice (rightmost group of symbols). EC0371-treated bpk mice exhibit a significant decrease in one-kidney weight as a percentage of total body weight relative to untreated bpk mice.
Figure 10:
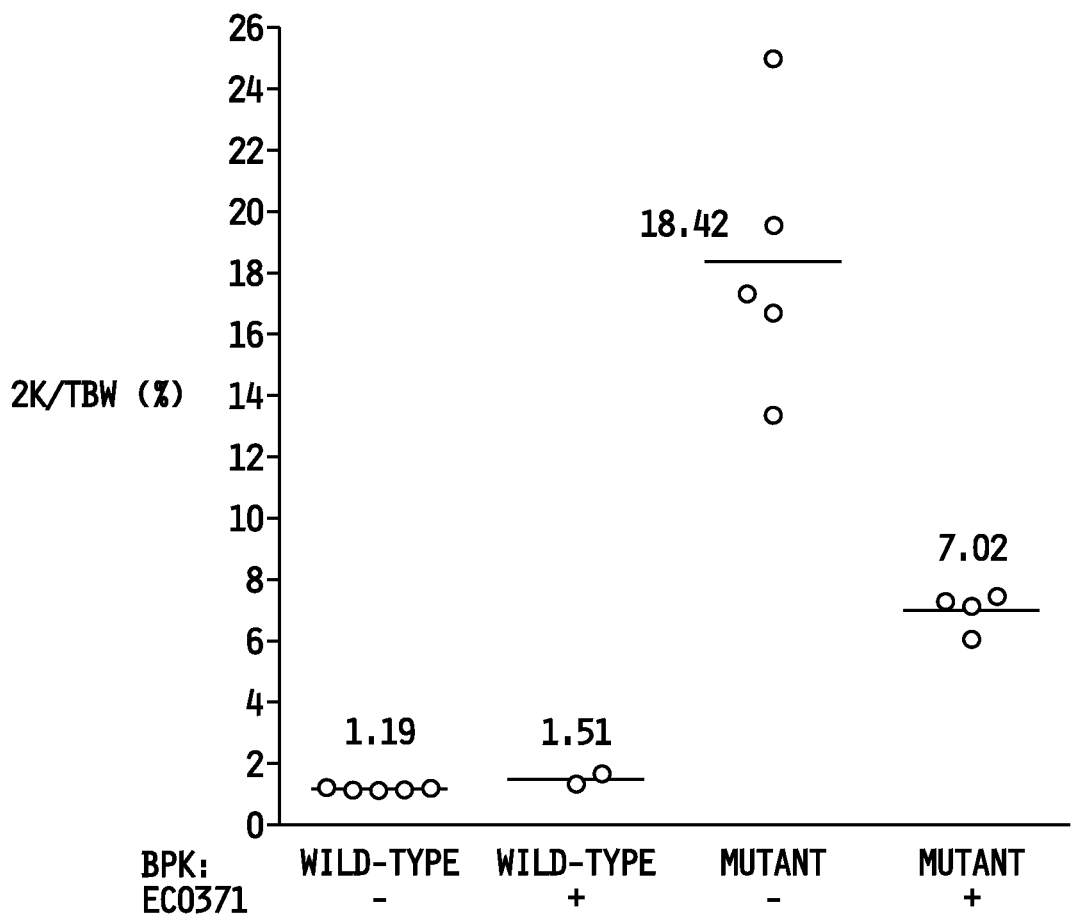
FIG. 10 shows the effect on two-kidney weight of EC0371 treatment in multiple bpk mutant mice (rightmost group of symbols). EC0371-treated bpk mice exhibit a significant decrease in two-kidney weight as a percentage of total body weight relative to untreated bpk mice.

EC0371 was prepared by reconstitution in sterile PBS to a concentration of 1 mM, then diluted 1:5 for a final concentration of 0.2 mM (2 nmol/µl). Mice were injected (i.p.) daily with either EC0371 (3 µmol/kg), vehicle (PBS), or received no injection, from postnatal day 7 to day 21. On day 21, whole body weight was recorded and blood was collected. Mice were then sacrificed and the kidneys, liver, spleen, and thymus were removed and weighed. EC0371 treatment of bpk-mutant mice was found to significantly improve the PKD phenotype as measured by kidney size (FIG. 8), and proportion of kidney(s) to whole body weight (FIGS. 9 and 10).

6. The compound of claim 4 having the formula
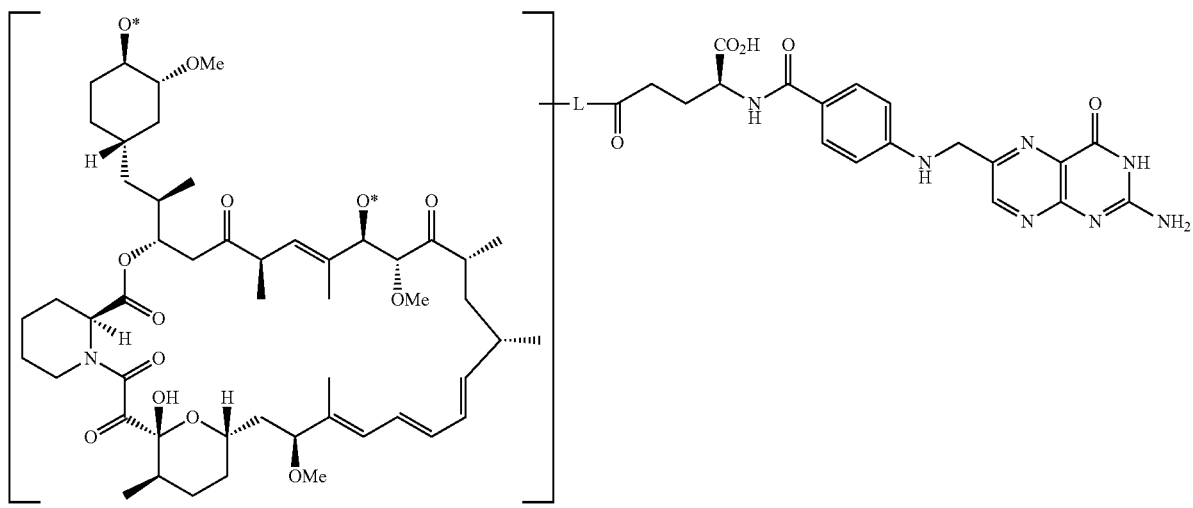
wherein L is connected to the rapamycin at either of (O*), and wherein R is hydrogen.
7. The compound of claim 3 having the formula
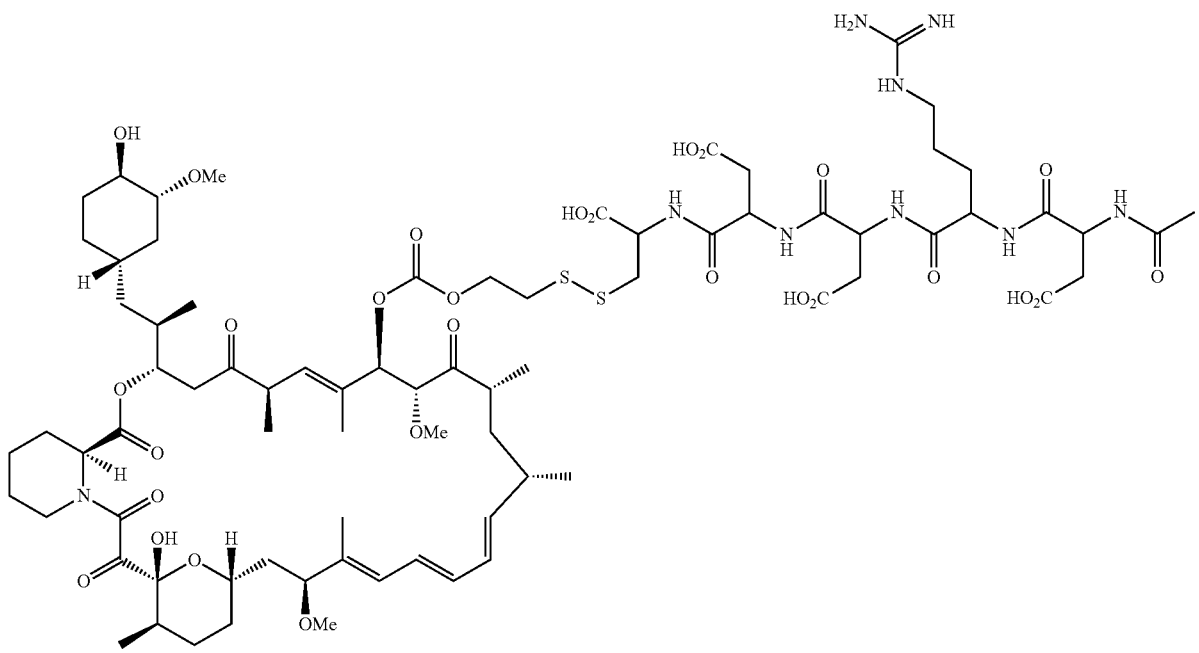
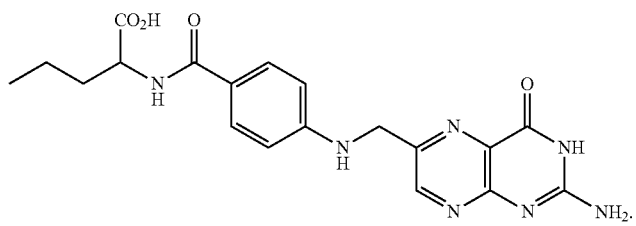

8. The compound of claim 3 having the formula
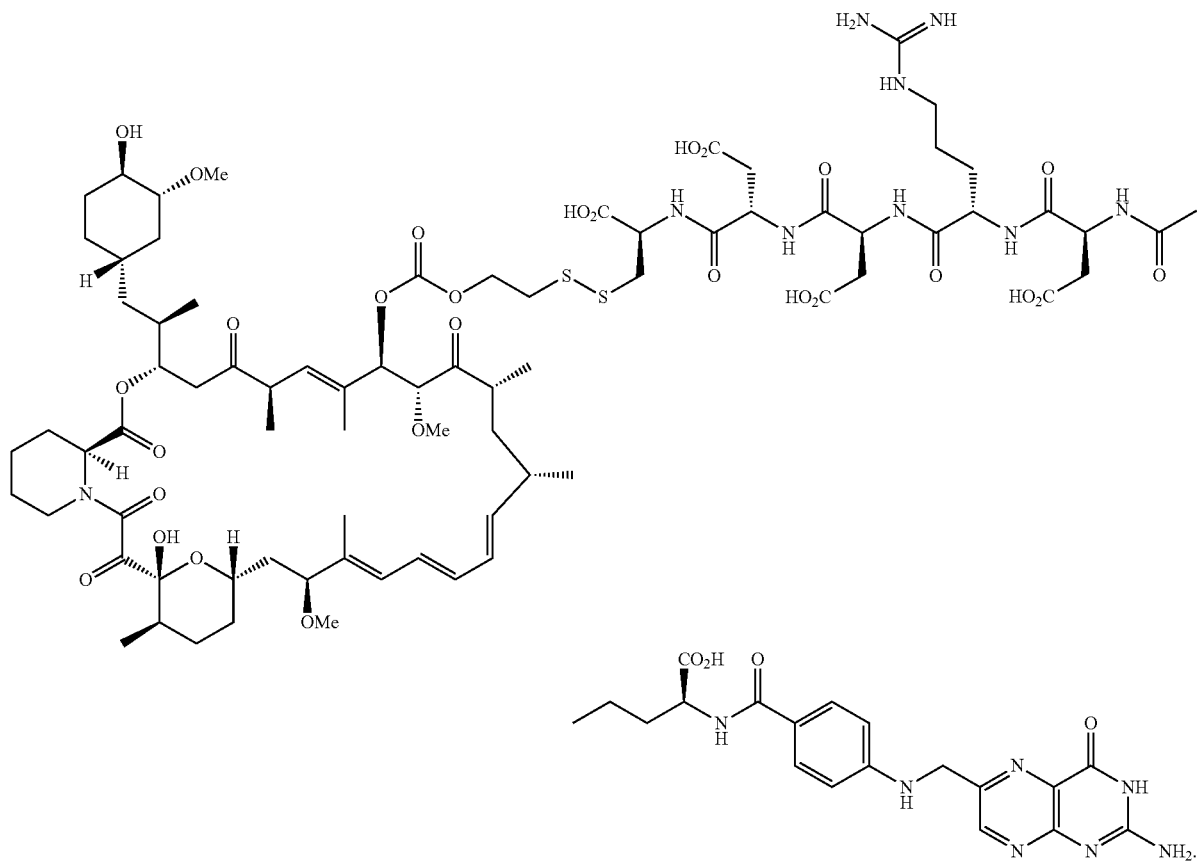

What is claimed is:

1. A method for treating a kidney disease state, said method comprising the steps of:
    administering to a patient suffering from the disease state an effective amount of a conjugate or complex of the general formula

V-L-D

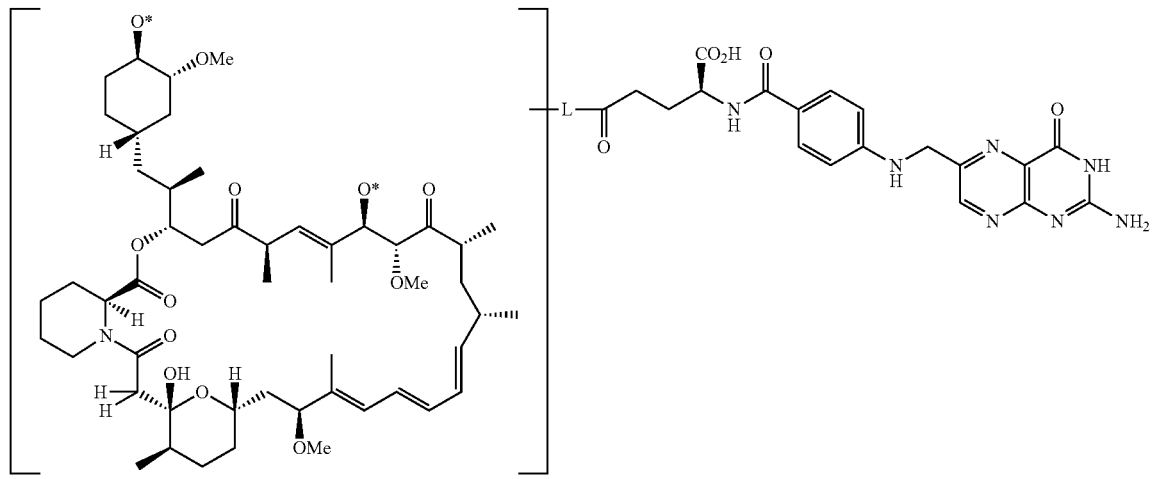

where V is folate, L is an optional linker, and D is rapamycin; and
    treating the disease state.

2. The method of claim 1 wherein the patient is suffering from a disease state selected from the group consisting of polycystic kidney disease, Dent's disease, nephrocytinosis, and Heymann nephritis.

3. A compound of the formula V-L-D, wherein V is folate, L is an optional linker, and D is a rapamycin.

4. The compound of claim 3 wherein V-L-D has the following formula:

where L, when present, is connected to the rapamycin at either of (O*), and the other of (O*) is substituted with R, wherein R is hydrogen or $-CO(CR^3R^4)_b(CR^5R^6)_d CR^7R^8R^9$; where $R^3$ and $R^4$ are each, independently, hydrogen, alkyl of 1-6 carbon atoms, alkenyl of 2-7 carbon atoms, alkynyl of 2-7 carbon atoms, trifluoromethyl, or F;

$R^5$ and $R^6$ are each, independently, hydrogen, alkyl of 1-6 carbon atoms, alkenyl of 2-7 carbon atoms, alkynyl of 2-7 carbon atoms, $(CR^3R^4)_fOH$, $CF_3$, F, or $CO_2R^{11}$;

$R^7$ is hydrogen, alkyl of 1-6 carbon atoms, alkenyl of 2-7 carbon atoms, alkynyl of 2-7 carbon atoms, $(CR^3R^4)_fOH$, $CF_3$, F, or $CO_2R^{11}$;

$R^8$ and $R^9$ are each, independently, hydrogen, alkyl of 1-6 carbon atoms, alkenyl of 2-7 carbon atoms, alkynyl of 2-7 carbon atoms, $(CR^3R^4)_fOH$, $CF_3$, F, or $CO_2R^{11}$;

$R^{11}$ is hydrogen, alkyl of 1-6 carbon atoms, alkenyl of 2-7 carbon atoms, alkynyl of 2-7 carbon atoms, or phenylalkyl of 7-10 carbon atoms;

b=0-6; d=0-6; and f=0-6.

5. The compound of claim 3 wherein the linker is a peptide comprising one or more amino acids selected from the group consisting of cysteine, aspartic acid, and arginine, where the amino acid is either in the D or the L configuration in each instance.